US009171483B2

(12) United States Patent
Cho

(10) Patent No.: US 9,171,483 B2
(45) Date of Patent: Oct. 27, 2015

(54) SYSTEM AND METHOD FOR PROVIDING LEARNING INFORMATION FOR VISUALLY IMPAIRED PEOPLE BASED ON HAPTIC ELECTRONIC BOARD

(75) Inventor: Jin-Soo Cho, Gyeonggi-do (KR)

(73) Assignee: GACHON UNIVERSITY INDUSTRY-UNIVERSITY COOPERATION (KR)

( * ) Notice: Subject to any disclaimer, the term of this patent is extended or adjusted under 35 U.S.C. 154(b) by 0 days.

(21) Appl. No.: 13/218,030

(22) Filed: Aug. 25, 2011

(65) Prior Publication Data
US 2012/0315605 A1   Dec. 13, 2012

(30) Foreign Application Priority Data

Jun. 8, 2011   (KR) ........................ 10-2011-0054861

(51) Int. Cl.
| | | |
|---|---|---|
| G09B 21/00 | (2006.01) | |
| G09B 21/02 | (2006.01) | |
| A61B 5/145 | (2006.01) | |

(52) U.S. Cl.
CPC .......... *G09B 21/005* (2013.01); *A61B 5/14532* (2013.01); *G09B 21/003* (2013.01); *G09B 21/004* (2013.01); *G09B 21/007* (2013.01); *G09B 21/008* (2013.01); *G09B 21/02* (2013.01)

(58) Field of Classification Search
CPC .. G09B 21/005; G09B 21/007; G09B 21/008; G09B 21/004; G09B 21/003; G09B 21/02
USPC ............. 434/114, 113, 115; 345/173; 348/51; 715/701; 341/21
See application file for complete search history.

(56) References Cited

U.S. PATENT DOCUMENTS

| 7,765,182 B2* | 7/2010 | Peurach et al. ............... 715/701 |
|---|---|---|
| 2003/0098803 A1* | 5/2003 | Gourgey et al. ............... 341/21 |

(Continued)

FOREIGN PATENT DOCUMENTS

KR    10-2010-0127077    12/2010

OTHER PUBLICATIONS

Nicotra et al., Innovative methods for Accessing mathematics by Visually Impaired Users, 2010, Springer.*

(Continued)

*Primary Examiner* — Sam Yao
*Assistant Examiner* — Eddy Saint-Vil
(74) *Attorney, Agent, or Firm* — Hershkovitz & Associates, PLLC; Abe Hershkovitz

(57) ABSTRACT

A system and method for providing learning information for visually impaired people based on a haptic electronic board is disclosed. The system for visually impaired people includes a learning information server in conjunction with a lecture and authoring program; a first information output device (PC) for receiving learning information for people with low vision from the learning information server through a wired/wireless network (LAN or WLAN) and having a viewer program for people with low vision, which is install therein, for providing functions of enlarging and reducing a screen; and a second information output device (haptic electronic board) for accessing to the learning information server through a local wireless network (ZigBee or Bluetooth) by using unique device IDs, converting learning information for blind people received from the learning information server to the haptic electronic board into haptic information, and transferring the haptic information to blind people.

10 Claims, 16 Drawing Sheets

(56) References Cited

U.S. PATENT DOCUMENTS

| | | | |
|---|---|---|---|
| 2005/0233287 A1* | 10/2005 | Bulatov et al. | 434/114 |
| 2011/0199321 A1* | 8/2011 | Kyung et al. | 345/173 |
| 2012/0070805 A1* | 3/2012 | Wong et al. | 434/114 |
| 2012/0257025 A1* | 10/2012 | Kim et al. | 348/51 |

OTHER PUBLICATIONS

Hernandez et al., Characterization of a Piezoelectric Ultrasonic Linear Motor for Bailie Displays, 2009, IEEE.*

Cha et al., A Framework for Haptic Broadcasting, 2009, IEEE.*

Yu et al., Evaluation of Multimodal Graphs for Blind People, 2003, Springer.*

Kyung et al., Haptic Stylus and Empirical Studies on Braille, Button and Texture Display, 2008, Journal of Biomedicine and Biotechnology.*

Texas Instruments, TSC2200 Touch Screen Controller Evaluation Module—User's Guide, 2002, Texas Instruments Incorporated.*

English Language Abstract of KR 10-2010-0127077.

\* cited by examiner implement a viewer function for people with low vision
(a) original video (b) enlarged video (c) color conversion
(d) black and white conversion (e) brightness increase (f) brightness decrease basic structure of array type piezoelectric actuator shapes of upper layer and lower layer of 8x2 module (left) and 8x2 standard graphic output module (a) educational information mixed with video and character (b) educational information based on character educational assistive engineering system based on graphic haptic electronic board

SYSTEM AND METHOD FOR PROVIDING LEARNING INFORMATION FOR VISUALLY IMPAIRED PEOPLE BASED ON HAPTIC ELECTRONIC BOARD

CROSS-REFERENCE TO RELATED APPLICATION

The present application claims the benefit under 35 U.S.C. §119(a) to a Korean patent application No. 10-2011-0054861, filed in the Korean Intellectual Property Office on Jun. 8, 2011 and the entire disclosure of which is incorporated herein by reference in its entirety.

This invention was made with Korean government support under Health Research and Development Projects awarded by Korean Ministry of Health and Welfare.

FIELD OF THE INVENTION

The present invention relates to a system and method for providing learning information for visually impaired people based on a haptic electronic board, and more particularly, to a system and method for providing learning information for visually impaired people based on a haptic electronic board, which stores learning information inputted by a lecturing and authoring program in a learning information server, converts the learning information into learning information for people with low vision and learning information for blind people, which may be transferred in a form of haptic information, in real time, simultaneously transmits through a wired/wireless network the learning information from a learning information server PC to a computer, in which a viewer program for people with low vision is installed, and to a plurality of haptic electronic boards for blind people, enlarges the learning information for people with low vision who different degrees of visual impairments have, or transfers the learning information for blind people to the blind people using the haptic electronic board in a form of the haptic information.

BACKGROUND OF THE INVENTION

G20 countries including Japan, USA, EU, and Republic of Korea, etc. have invested and made lots of efforts in order to improve an educational environment for visually impaired people in government, private industry, research laboratories, etc., and have been continuously made a greater efforts to improve the educational environment for visually impaired people by developing various types of educational assistive engineering devices for visually impaired people.

Conventional educational assistive engineering devices for the visually impaired people were the level which is simply enlarged character information and provided to people with low vision by using a large monitor, a screen enlargement program, a voice recorder capable of making a memo related to voice, voice output software, a braille information terminal, a braille printer, a document cognition terminal, and an enlargement reader.

Recently, educational assistive technology apparatuses have been improved to the level of converting character information into braille or voice and providing blind people with the converted braille or voice by using technologies such as an OCR (Optical Character Reader), a TTS (Text to Speech) system, a braille translator (translating a text to braille), and a reverse braille translator such as a braille information terminal, voice output software and a document cognition program and the like.

According to a survey on the employment status of visually impaired people, among those who desire vocational training, 12.2% (57,546 out of total 472,514, in 2005 year) are engaged in massage, acupuncture, clergy, fortune telling, and teacher. This situation shows that a tendency for visually impaired people to enter the workforce is very limited up to now. The current status implies that the special educational environment is not suitable for the visually impaired people who desire to work for various fields. Accordingly, more specialized educational assistive engineering devices for improving a learning efficiency of the visually impaired people are required.

There is no educational assistive engineering device for simultaneously transmitting educational data such as visual character or video information in real time in a current special education environment for visually impaired people since educational equipment such as a blackboard used in a general education environment is also used in the special education environment. Therefore, visually impaired people need to receive learning information in a form of haptic information and voice information in the special education environment of visually impaired people.

However, the haptic information and the voice information are factors which heavily restrict an amount of information which may be conveyed for a limited education time. Although visually impaired people may be able to easily understand the information when video information is converted to haptic information and then the converted haptic information is provided to the visually impaired people, there is currently no assistive engineering device for automatically converting the video information into the haptic information in real time.

Specifically, people with low vision and blind people receive an education together in the current special education environment for visually impaired people based on characters or voice, and there is no method of converting suitable educational data and video data in real time according to the degrees of visual impairments and then transmitting the converted data.

For example, people with low vision may acquire educational information by using a screen enlargement program. Blind people may acquire educational information by using braille or the sense of touch. However, in the current special education environment in which people with low vision and blind people study together, there is a limitation in suitably converting and providing the educational information according to an information cognition characteristic for each visual impairment rating and then providing the converted information within a limited education time.

The current special education environment based on only characters and voice makes visually impaired people feel many difficulties in acquiring necessary knowledge. As a result, visually impaired people have been appeared a phenomenon which avoid entering a school requiring a high level of knowledge.

When visually impaired people acquire educational data by using haptic information converted from video information, the visually impaired people may easily understand the information, but the amount of haptic information converted from video information is extremely limited in the current special education environment of visually impaired people. However a braille printer and educational equipment for converting the video information into the haptic information exist, there is a practical limitation in terms of time and costs because the video information should be manually converted to the haptic information and manufactured by a special education instructor or an assistant.

According to the current status, an educational assistive engineering device for converting the learning data in a form of a character, a picture, a figure, and an image into the haptic information in real time and then simultaneously transmitting the converted haptic information to the visually impaired people is strongly required in order to provide a special learning environment for the visually impaired people as similar as possible to the general learning environment.

SUMMARY OF THE INVENTION

To address the above-discussed deficiencies of the prior art, it is a primary object to provide a learning information providing system for visually impaired people based on a haptic electronic board, wherein the system inputs learning information including equation, symbol, picture, figure, graph, and image information as well as character information written by a lecturing and authoring program to a learning information server, re-configures the learning information to image information for people with low vision in order to enable the people with low vision to easily recognize the learning information, automatically converts the learning information into haptic information for blind people, which the blind people can easily recognize the learning information, in real time, transmits the learning information stored in the learning information server to first information output devices (PCs) for people with low vision, in which a viewer program for people with low vision is installed, and to second information output devices (haptic electronic boards) for blind people through a wired/wireless network in real time, and provides both people with low vision and blind people with suitable learning information.

Another aspect of the present invention is to provide a method for providing learning information for visually impaired people based on a haptic electronic board.

In accordance with an aspect of the present invention, a system for providing learning information for visually impaired people based on a haptic electronic board, the system comprises: a first information output device which is a PC for people with low vision for accessing to a learning information server in conjunction with a lecturing and authoring program to receive learning information for people with low vision, wherein said first information output device includes a LAN or WLAN communication unit and having a viewer program for people with low vision installed therein and provides functions of information enlarging, reducing and shifting, color adjusting and brightness adjusting; and a second information output device which is a haptic electronic board for blind people for accessing to the learning information server through a local wireless network of used for local wireless communication using a unique device ID assigned thereto, receiving learning information for blind people from the learning information server, converting the learning information for blind people into haptic information, controlling probes of a plurality of Tiny Ultrasonic Linear Actuators disposed in a multi-arrangement, outputting the haptic information to a graphic output module, and transferring the haptic information to visually impaired people, wherein the lecturing and authoring program and the learning information server are installed in a learning information server PC equipped with a network connection unit using LAN or WLAN and a wireless communication interface unit using the local wireless network, and the learning information server provides a function of inputting a character and an equation, a writing function, a function of drawing a graph and a figure, a function of retrieving existing data associated with learning information inputted from an input device by the lecturing and authoring program referred to as a "haptic edu", converting learning information into learning information for people with low vision including character, equation, symbol, figure, graph, and image information produced by the functions, or learning information for blind people, which may be transferred in a form of haptic information by using an automatic haptic information conversion technology, and transmitting the learning information for people with low vision or the learning information for blind people, which can be transferred as haptic information, to one or more information output devices through a wired/wireless network using LAN or WLAN or a local wireless network in a 1:N or a 1:1 transmission mode, wherein the lecturing and authoring program and the learning information server designate a page of learning data for visually impaired people by synchronizing with a page of specific learning information based on identical learning information by the lecturing and authoring program, or synchronize with a learning page by transmitting information of a current page to the learning information server by the people with low vision or the blind people, wherein said second information output device includes a communication unit for receiving the learning information for blind people from the learning information server through the local wireless communication using local wireless network; a master board for receiving the learning information for blind people from the communication unit to provide a control command, and including an MCU; at least one slave board for receiving the control command from the master board, and controlling ultrasonic actuators arranged in a multi-arrangement, and being connected with the master board through an SPI bus; a plurality of Tiny Ultrasonic Linear Actuators disposed in a multi-arrangement; and a step down DC-DC converter for being supplied with a power supply, converting a DC-DC voltage, and providing the converted DC-DC voltage to the master board and the slave board, wherein a distance between probes of the TULA of the graphic output module of said second information output device is set to a value lower than 2.7 mm in order to enable the blind people to accurately recognize the learning information for blind people including braille, equation, symbol, figure, graph, and image information for blind people as the haptic information, and wherein a module of an array type piezoelectric actuator is manufactured such that it has a multi-structure in order to improve an accuracy of the array type piezoelectric module.

In accordance with another aspect of the present invention, a method for providing learning information for visually impaired people based on a haptic electronic board, the method comprises the steps of: providing a function of inputting a character and an equation, a writing function, a function of drawing a graph and a figure, a function of retrieving existing data, inputting learning information for visually impaired people to a learning information server by using a lecturing and authoring program, distinguishing first information output devices accessed through a wired/wireless network to the learning information server by their IP addresses, and distinguishing second information output devices accessed through a local wireless network to the learning information server by their device IDs; identifying a kind of network that is LAN/WLAN or the local wireless network accessing the learning information server, and determining whether a user is a person with low vision; as a result of the determination, when a first information output device for people with low vision accesses to the learning information server, converting inputted learning information into learning information for people with low vision by using an information converting unit, and transmitting the learning information for people with low vision from the learning information server to the first information output device through the wired/wireless network using LAN or WLAN; as a result of the determination, when a second information output device for blind people accesses to the learning information server, converting inputted learning information into haptic information for blind people, and transmitting the learning information for blind people, which can be transferred as the haptic information, from the learning information server to the second information output device that is haptic electronic board through the local wireless network; and designating a page of learning data for visually impaired people by synchronizing with a page of specific learning information based on identical learning information by the lecturing and authoring program, or synchronizing with a learning page by transmitting information of a current page to the learning information server by the people with low vision or the blind people.

The method for providing learning information for visually impaired people based on a haptic electronic board further comprises a step of converting the learning information for blind people received from the learning information server into the haptic information, controlling probes of a plurality of Tiny Ultrasonic Linear Actuators disposed in a multi-arrangement, outputting the haptic information to a graphic output module, and transferring the haptic information to the blind people using the graphic haptic electronic board in the second information output device.

In accordance with still another aspect of the present invention, a non-transitory computer-readable storage medium having a program recorded thereon; where the program is executed by a computer processor configured to: (a) inputting a character and an equation, a writing function, a function of drawing a graph and a figure, a function of retrieving existing data by using a lecturing and authoring program, inputting learning information for visually impaired people to a learning information server, distinguishing first information output devices accessed through a wired/wireless network to the learning information server by their IP addresses, and distinguishing second information output devices accessed through a local wireless network to the learning information server by their device IDs; (b) identifying a kind of network that is LAN/WLAN or the local wireless network accessing the learning information server, and determining whether a user is a person with low vision or not; (c) as a result of the determination, when a first information output device for people with low vision accesses to the learning information server, converting inputted learning information into learning information for people with low vision by using an information converting unit, and transmitting the learning information for people with low vision from the learning information server to the first information output device through the wired/wireless network using LAN or WLAN; (d) as a result of the determination, when a second information output device for blind people accesses to the learning information server, converting inputted learning information into haptic information for blind people, and transmitting the learning information for blind people, which can be transferred as the haptic information, from the learning information server to the second information output device that is haptic electronic board through the local wireless network; and (e) designating a page of learning data for visually impaired people by synchronizing with a page of specific learning information based on identical learning information by the lecturing and authoring program, or synchronizing with a learning page by transmitting information of a current page to the learning information server by the people with low vision or the blind people.

BRIEF DESCRIPTION OF THE DRAWINGS

The above and other aspects, features and advantages of certain exemplary embodiments of the present invention will be more apparent from the following detailed description taken in conjunction with the accompanying drawings, in which.

DETAILED DESCRIPTION OF THE INVENTION

Hereinafter, the exemplary embodiments of the present invention will be described in detail with reference to the accompanying drawings.

Figure 1:
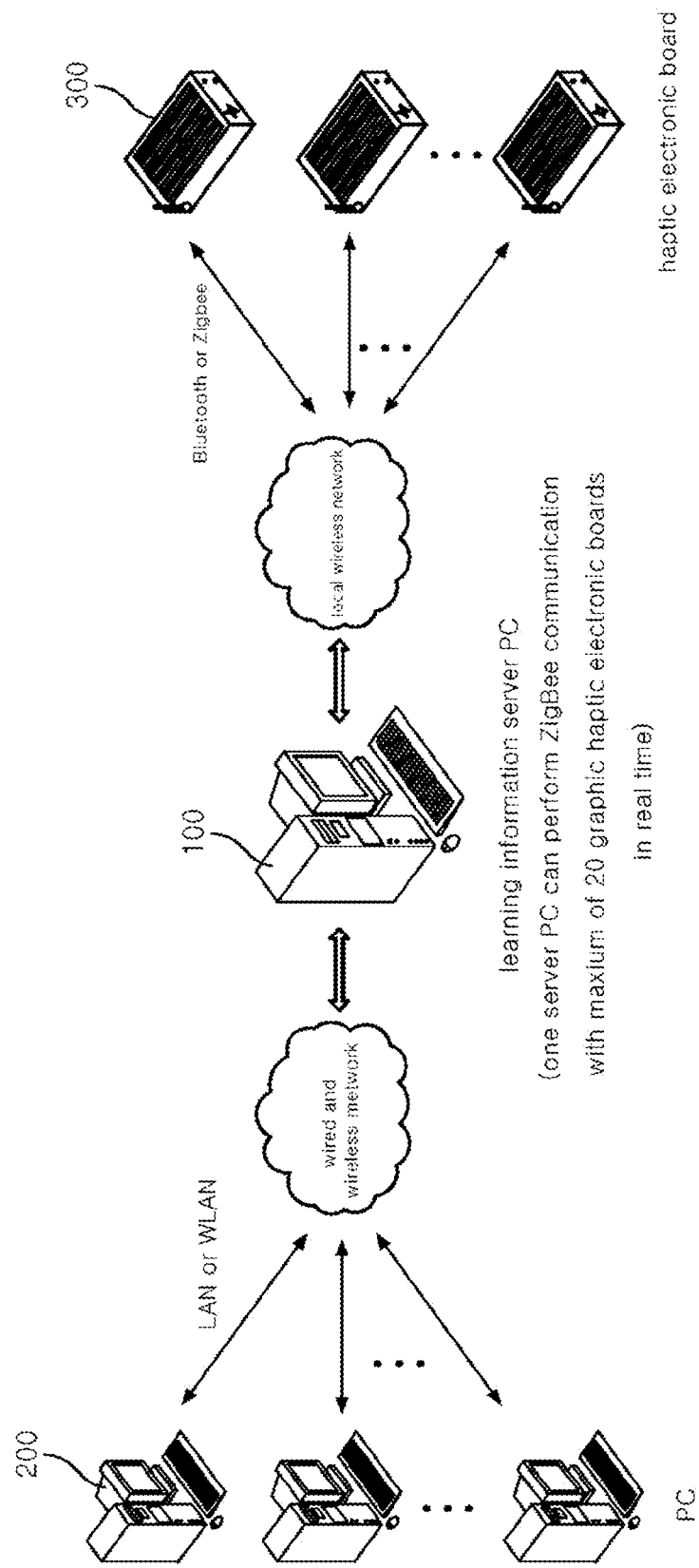
FIG. 1 is a diagram illustrating a network of a system for providing learning information for visually impaired people using a terminal, in which a viewer program for people with low vision is installed, and a haptic electronic board for blind people according to the present invention.

FIG. 1 is a diagram illustrating a network of a system for providing learning information for visually impaired people using a terminal in which a viewer program for people with low vision is installed, and a haptic electronic board for blind people according to the present invention.

The system for providing learning information for visually impaired people is installed in a server PC equipped with a network connection unit (LAN or WLAN) and a wireless communication interface unit (ZigBee or Bluetooth).

The system for providing the learning information for visually impaired people includes a learning information server 100, a first information output device (PC) 200 for people with low vision, and a second information output device (haptic electronic board) 300 for blind people.

The learning information server 100 provides a function of inputting a character and a number, a writing function, a function of drawing a graph and a figure, and a function of retrieving existing data, converts learning information input from an input device into learning information for people with low vision including character, number, symbol, figure, graph, and image information produced by the above functions or into learning information for blind people, which may be transferred in a form of haptic information by using an automatic haptic information conversion technology, and transmits the learning information for people with low vision or the learning information for blind people, which may be transferred in a form of haptic information, to at least one information output devices through a wired/wireless network (LAN or WLAN) or a wireless network (ZigBee or Bluetooth) in a 1:N or a 1:1 transmission mode.

The first information output device (PC) 200 for people with low vision includes a LAN or a WLAN communication unit, accesses to the learning information server PC in conjunction with the lecturing and authoring program to receive the learning information for people with low vision by using TCP/IP, and has a viewer program for people with low vision installed therein.

The second information output device (haptic electronic board) 300 for blind people assigns a unique device ID, accesses to the learning information server PC through a wireless network (ZigBee or Bluetooth) by using the inherent device ID to receive the learning information for blind people from the learning information server 100, converts the learning information for blind people into haptic information, controls probes of a plurality of Tiny Ultrasonic Linear Actuators (TULAs) in a multi-arrangement, outputs the haptic information to a graphic output module, and transfers the haptic information related to the learning information for blind people to the visually impaired people.

The first information output device (PC) 200 uses computers such as a PC (Personal computer), a laptop computer, and so forth, has the viewer program for people with low vision installed therein and accesses to the learning information server 100 through the wired/wireless network (LAN or WLAN).

The second information output device (haptic electronic board) 300 assigns a unique device ID, uses a graphic haptic electronic board for blind people, accesses to the learning information server 100 through local wireless communication (ZigBee or Bluetooth) to convert the learning information for blind people into haptic information through the local wireless network (ZigBee or Bluetooth), controls the probes of a plurality of Tiny Ultrasonic Linear Actuators (TULAs) in a multi-arrangement, outputs the haptic information to the graphic output module, and transmits the haptic information to the blind people.

Figure 2:
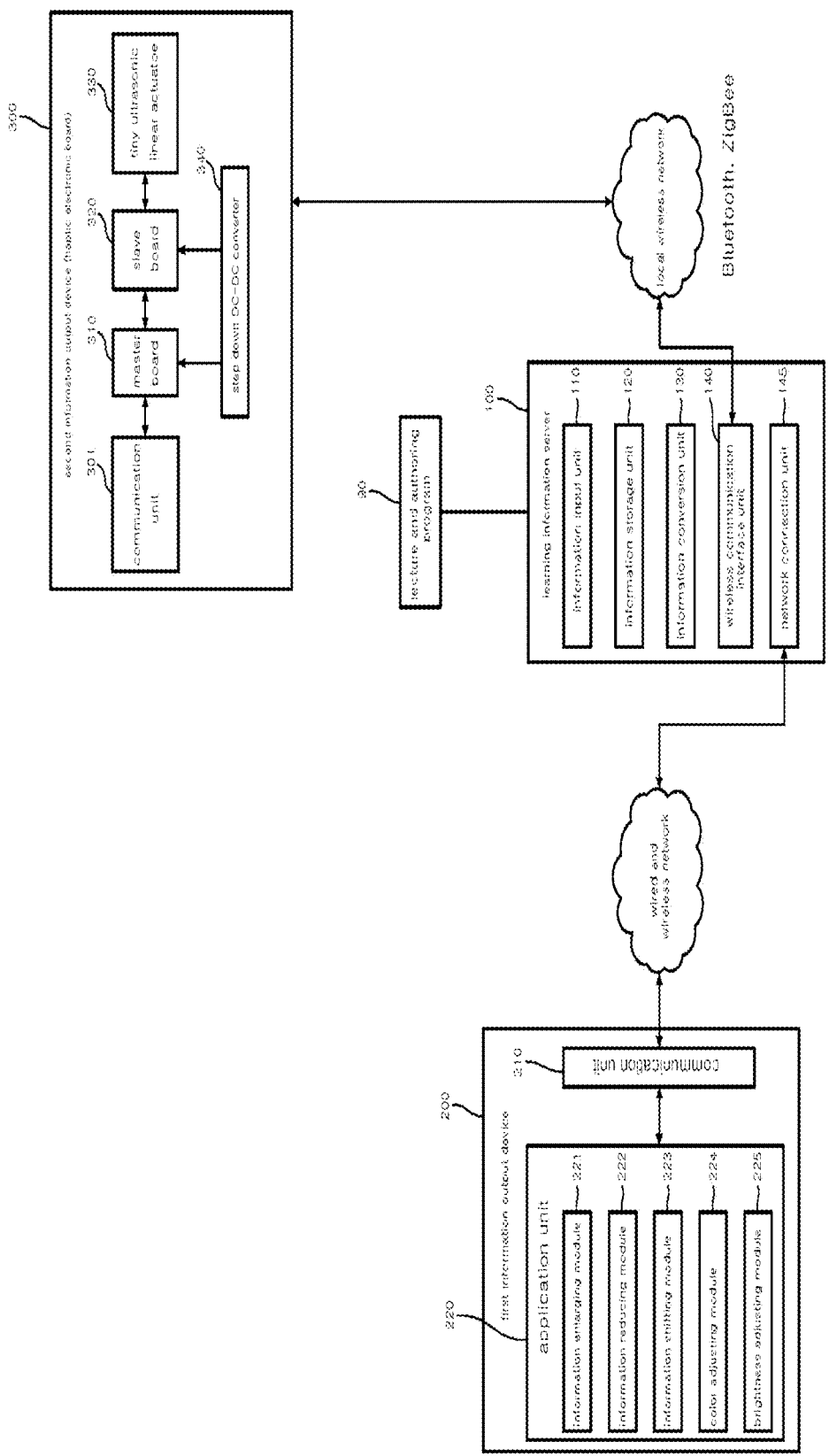
FIG. 2 is a block diagram illustrating in detail a system for providing learning information for visually impaired people using a terminal in which a viewer program for people with low vision is installed and a haptic electronic board for blind people according to an embodiment of the present invention.

FIG. 2 is a block diagram illustrating in detail a system for providing learning information for visually impaired people using a terminal in which the viewer program for people with low vision is installed, and the haptic electronic board for blind people according to an embodiment of the present invention.

The lecturing and authoring program 90 provides a function of inputting a character and a number, a writing function, a function of drawing a graph and a figure, and a function of retrieving existing data, converts the learning information inputted from an input device into learning information for people with low vision including an authorized character, number, symbol, figure, graph, and image information produced through the above functions or into learning information for blind people which may be transferred in a form of the haptic information by using an automatic haptic information conversion technology, and manages sessions of accessed clients. Also, the lecturing and authoring program 90 provides a function of monitoring an access state, a function of monitoring a current view page of an accessed student, and a function of designating a learning page.

The learning information server 100 is received specific learning information for visually impaired people including number, symbol, picture, figure, graph, and image information as well as character information produced by the lecturing and authoring program 90, and re-configures the learning information for people with low vision by the lecturing and authoring program 90 in which a touch algorithm of video information is implemented, in order to enable the people with low vision to easily recognize the learning information, automatically converts the learning information into haptic information, which may be transferred in a form of the haptic information in order to enable the blind people to easily recognize the learning information, analyzes device IDs of accessed information output devices so as to classify their IDs according to a visual impairment characteristic, and simultaneously transmits each of the learning information for people with low vision and the learning information for blind people from the learning information server 100 to a plurality of accessed first information output devices (PCs) 200 or a plurality of accessed second information output devices (haptic electronic boards) 300 respectively through a wired/wireless network (LAN or WLAN) and/or a local wireless network (ZigBee or Bluetooth).

One learning information server PC includes a network connection unit 145 communicating with the first information output devices (PCs) 200 in which the viewer program for people with low vision is installed through the wired/wireless network (LAN or WLAN), and a wireless communication interface unit 140 communicating with the second information output devices (graphic haptic electronic boards) 300 for blind people through the local wireless network (ZigBee or Bluetooth). The one learning information server PC can transmit the learning information for visually impaired people to a maximum of twenty information output devices (graphic haptic electronic boards) 300 for blind people by using the local wireless communication having a small power consumption and an excellent communication stability, and is possible a bidirectional communication between the learning information server 100 and the second information output devices 300.

The one learning information server PC transmits the learning information for people with low vision to the first information output devices (PCs or laptop computers) 200 in which the viewer program for people with low vision is installed, by using TCP/IP as the wired/wireless network (LAN or WLAN), and transmits the learning information for blind people to the second information output devices (graphic haptic electronic boards) 300 for blind people by using the wireless network (ZigBee or Bluetooth).

The first information output devices (PCs or laptop computers) 200 for people with low vision include a LAN or a WLAN communication unit 210. The second information output devices (haptic electronic board) 300 for blind people include a ZigBee communication unit or a Bluetooth communication unit 301.

When the ZigBee communication is used, the ZigBee communication unit 301 of the second information output devices (haptic electronic boards) 300 uses a DS-SS (Direct Sequence-Spread Spectrum) modem and has a frequency band of 2.4 GHz, 862-868 MHz, or 915 MHz, provides a maximum data rate of 250 kbps, and communicates with the learning information server PC equipped with a ZigBee communication interface by using the local wireless communication in a range of 20-30 m in a classroom in a P2P Star Mesh topology.

When the Bluetooth communication is used, the Bluetooth communication unit (slave) 301 of the second information output devices (haptic electronic boards) 300 communicates with the learning information server PC equipped with a Bluetooth communication interface (master) by using the local wireless communication in a range of 100 m in a classroom with a 2.4 GHz frequency band.

The learning information for blind people inputted to the learning information server 100 by an input device (keyboard or mouse) is transmitted to the first information output device 200 through the wired/wireless network (LAN or WLAN) and the second information output device 300 through the local wireless network (ZigBee or Bluetooth) generally in a 1:N transmission mode, or may be transmitted in a 1:1 transmission mode by selecting a device ID for each information output device, if necessary.

Referring to FIG. 2, the system for providing the learning information for visually impaired people according to the present invention includes the first information output device 200 for receiving an input of specific learning information for visually impaired people including number, equation, picture, figure, graph, and image information as well as character information from an information input unit 110 and stores them in the learning information server 100, re-configuring the input learning information to the learning information for people with low vision by the lecturing and authoring program in which a touch algorithm of the video is implemented, automatically converting the input learning information to learning information, which may be transferred in a form of the haptic information, in real time in order to enable the blind people to easily recognize, and simultaneously transmitting the learning information for people with low vision and the learning information for blind people to the information output devices from the learning information server 100 through the network, and outputting the learning information for people with low vision received through the wired/wireless network (LAN or WLAN) and having a viewer program for people with low vision installed therein; and the second information output device (haptic electronic board) 300 for blind people including the ZigBee or the Bluetooth communication unit for receiving the learning information for blind people, converting the learning information for blind people into the haptic information, and transferring the haptic information to the blind people.

The learning information server 100 includes an information input unit 110 for receiving an input of specific learning information for visually impaired people including equation, symbol, figure, graph, and image information as well as character information produced by the lecturing and authoring program; an information storing unit 120 for storing the information inputted from the information input unit 110; an information conversion unit 130 for converting the learning information inputted from the information input unit 110 to the learning information for people with low vision and the learning information for blind people, which may be transferred in a form of the haptic information; a wireless communication interface unit 140 for providing the learning information for blind people when the learning information server 100 communicates with a plurality of second information output devices 300 through the local wireless network (ZigBee or Bluetooth); and a network connection unit 145 for transmitting the learning information for people with low vision to the first information output device 200 in which the viewer program for people with low vision is installed, when the learning information server PC communicates with the first information output devices 200 through the wired/wireless network (LAN or WLAN).

The first information output device 200 has the viewer program for people with low vision installed therein, receives the learning information for people with low vision from the learning information server 100 through the wired/wireless network (LAN or WLAN), sets a size, a brightness, and a contrast of a screen and enlarges a screen size according to sights of the people with low vision by using the viewer program for people with low vision, and outputs the learning information for people with low vision.

As an embodiment of the second information output device (haptic electronic board) 300, a 64×64 graphic output module has been developed, in which the surface texture and the probe height of the module have been set after testing by real users. As a result, a standard graphic output module having an array including a total of 4096 probes (pins) has been developed.

The second information output device (haptic electronic board) 300 basically provides a UART (Universal Asynchronous Receiver/Transmitter) interface connected to a PC, and the ZigBee interface or the Bluetooth interface has been developed so as to implement the present invention. A real time graphic haptic electronic board considers a control factor and an optimal controllability of Tiny Ultrasonic Linear Actuators (TULAs) in a multi-arrangement which enables a linear motion by reducing a size of a driving circuit using an FPGA (Field Programmable Gate Array) and developing a program for simultaneously controlling a driving frequency and a phase difference, analyzes a tactile perception characteristic for a character, an equation, a number, a symbol, a figure, a graph, and an image included in the learning information for blind people through an experiment, and outputs the analyzed tactile perception characteristic to the graphic output unit.

The second information output device (haptic electronic board) 300 provides a graphic output function or a braille scroll function by using top, bottom, left, right, front, and rear user input buttons, and is configured so that its screen can be moved to a next screen or a previous screen, which improves the convenience of a user and implements a reset function and a reload function of the graphic output unit.

The second information output device (haptic electronic board) 300 provides a function of scrolling the haptic information associated with an image and braille and a function of scrolling the haptic information for a limited resolution and a divided video data of the haptic electronic board according to an input of a user of the haptic electronic board. The learning information server 100 stores the learning information outputted to the second information output device (haptic electronic board) 300 connected to the learning information server 100, and controls each of the information output devices.

Figure 3:
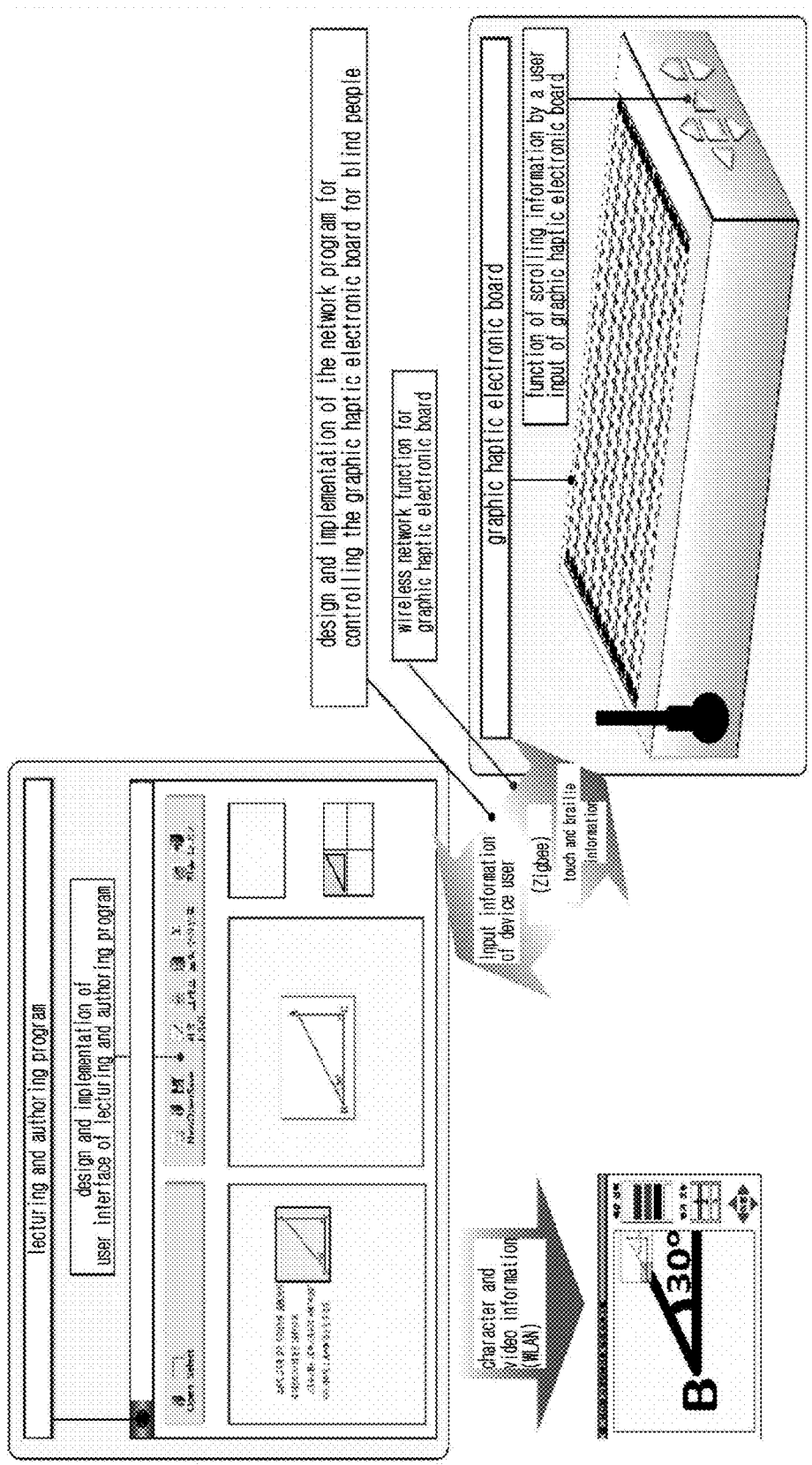
FIG. 3 is a screen illustrating constructions of a lecturing and authoring program (haptic edu) for teachers, the viewer program for people with low vision, and the haptic electronic board for blind people for a learning information system for visually impaired people according to the present invention.

FIG. 3 is a screen illustrating constructions of the lecturing and authoring program (haptic edu) for teachers, the viewer program for people with low vision, and the haptic electronic board for blind people for the learning information system for visually impaired people according to the present invention.

The lecturing and authoring program (hereinafter referred to as a "haptic edu") for teachers of the learning information server 100 does not discriminate between the produced lecture data for blind people and for people with low vision. Instead, the lecturing and authoring program converts the produced lecture data into data suitable for each of the information output devices and transmits the converted data to the first information output devices 200, which can simultaneously communicate in real time and have the viewer program for people with low vision, and the second information output devices (haptic electronic board for blind people) 300 using the local wireless communication (ZigBee or Bluetooth).

The lecturing and authoring program (haptic edu) of the learning information server 100 is educational assistive engineering software for converting the same learning data into data suitable for each of the visual impairment characteristics, and transmitting the converted learning data to both people with low vision and blind people in real time.

The lecturing and authoring program (haptic edu) does not directly produce separate learning data for people with low vision and for blind people, but produce one learning data and then separately produce the learning data for people with low vision and the learning data for blind people by using the same learning data. The graphic haptic electronic board is an educational assistive engineering system for converting the learning information for blind people into haptic information and transferring the haptic information to the blind people.

The learning information server 100 simultaneously provides the learning information for people with low vision to the first information output device (PC or braille terminal) in which the viewer program for people with low vision is installed, and/or the learning information for blind people to the second information output device (haptic electronic board) 300 for blind people.

The lecturing and authoring program (haptic edu) recognizes the haptic information related to a character, a number, an equation, a symbol, a figure, and a graph according to a characteristic of the second information output device (haptic output device) 300, and particularly, enables the blind people to effectively recognize the haptic information related to the image information by implementing a touch algorithm of the image.

When the lecturing and producing program (haptic edu) converts the learning information into the learning information for blind people, which is input suitable for a resolution of the second information output device (haptic electronic board) 300 and may be transferred in a form of haptic information, to transmit the converted learning information to the second information output devices (haptic electronic board) 300, the second information output devices (haptic electronic board) 300 receive the learning information for blind people through the local wireless communication (ZigBee or Bluetooth) and convert the learning information for blind people into the haptic information. As a result, the blind people may recognize the haptic information related to learning information through their sense of touch by hands.

The lecturing and authoring program (haptic edu) executes a function of generating a graph, a function of inputting and converting an equation, a function of automatically converting braille, a function of managing students, and a function of storing and retrieving prepared data in consideration of characteristics of main subjects for blind people and a writing function, which can be used as a teacher writes on a blackboard.

The lecturing and authoring program (haptic edu) controls access states, and functions of monitoring an enlarged output screen, transmitting individual learning data, and controlling to designate a current output screen of the second information output device (haptic electronic board) 300 for blind people accessed through the local wireless communication (ZigBee or Bluetooth) and the first information output device 200 for people with low vision. The viewer program for people with low vision of the first information output device 200 and the second information output device (haptic electronic board) 300 are controlled by the lecturing and authoring program (haptic edu), and the lecturing and authoring program (haptic edu) provides an automatic switch function of switching a screen of a user to a learning data screen controlled by a teacher.

The viewer program (client) for people with low vision of the first information output device 200 receives the learning data of teachers from the learning information server 100 through the wired/wireless network (LAN or WLAN), sets functions of outputting a character, a number, an equation, a symbol, a figure, a graph, and an image, and functions of selecting a video size, selecting a color, adjusting a brightness, and controlling a contrast according to sights of the people with low vision, and then enlarges or reduces a screen according to sights of the people with low vision, so that the viewer program (client) for people with low vision enables the people with low vision to recognize the learning information for people with low vision.

The learning information server 100 designs and implements a network program for controlling the learning information for people with low vision, controls each of the viewer programs (clients) for people with low vision set with inherent identification codes, and transmits the learning information for people with low vision including character, number, equation, symbol, figure, graph, and image information produced by determining the viewer program for people with low vision. The learning information for people with low vision produced by the lecturing and authoring program is transmitted in a 1:N mode, or selectively transmitted to each of the first information output devices in a 1:1 mode, if necessary.

The second information output device (haptic electronic board) 300 receives the learning information for blind people from the learning information server 100 through the local wireless communication (ZigBee or Bluetooth), converts the received learning information for blind people into the haptic information, controls protrusions of the probes of the TULAs in a multi-arrangement, outputs the haptic information to the graphic output module, and changes a page or executes a page changing command in the lecturing and authoring program by using buttons of the haptic electronic board for blind people.

The lecturing and authoring program (haptic edu) provides a function of inputting a letter including inputs of a character, an equation, a symbol, and a figure; a function of inputting a detailed description and an annotation for a specific region of the produced video information with a letter; a function of automatically translating braille for blind people; a function of implementing a touch algorithm of a video suitable for the second information output device (haptic electronic board) 300 for blind people; a free drawing function by using an input device such as a mouse or a tablet PC, a drawing function using a template of frequently used figures such as a straight line, a triangle, a circle, and a graph, a function of setting a unit of a two dimensional coordinate system, a function of directly drawing image information providing a function of drawing a function and a graph; a preview function and a region division function of identifying a type of the haptic information, which will be output to the graphic output module of the second information output device (haptic electronic board) 300, by a producer in advance and directly dividing a region of the image data by the producer and transmitting the divided region when a size of the image information to be transmitted is large or a resolution of the image information to be transmitted is high; and a function of storing and retrieving the produced learning information.

The viewer program for people with low vision is used for the first information output device 200, implements necessary functions such as functions of dividing and magnifying the screen size, and moving a screen, a function of selecting a color, a function of adjusting a brightness, etc., and provides the people with low vision with the learning information for people with low vision including character, symbol, equation, figure, graph, and image information received from the learning information server 100.

Figure 4:
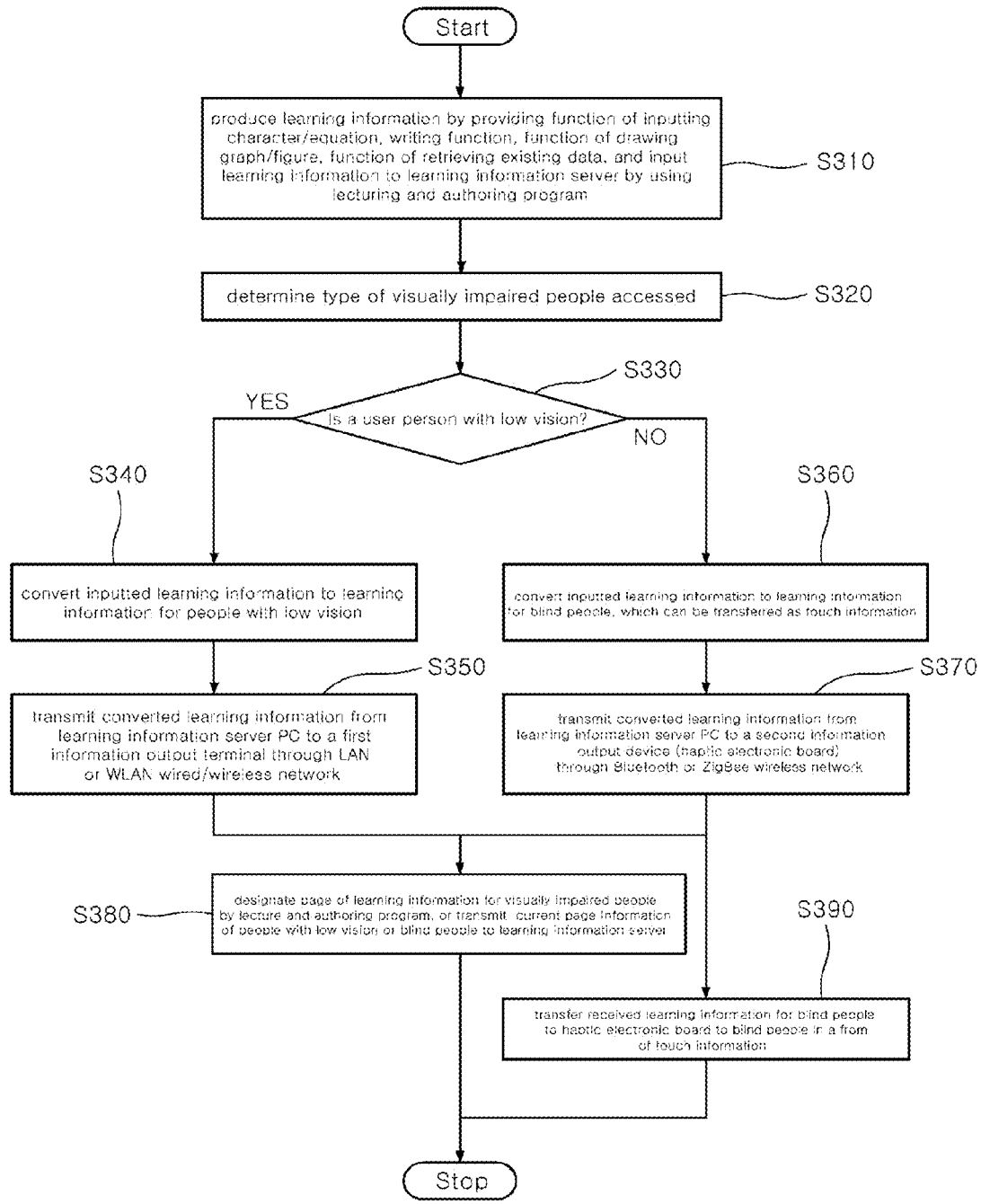
FIG. 4 is a flowchart illustrating a method for providing learning information for visually impaired people based on the terminal, in which the viewer program for people with low vision is installed, and the haptic electronic board for blind people according to the present invention.

FIG. 4 is a flowchart illustrating a method for providing the learning information for visually impaired people based on the viewer program for people with low vision and the haptic electronic board for blind people according to the present invention.

A teacher inputs the learning information for visually impaired people to the learning information server 100 by using the lecturing and authoring program providing a function of inputting a character and an equation, a writing function, a function of drawing a graph and a figure, and a function of retrieving existing data (S310). Then, the learning information server 100 discriminates the first information output devices 200 which are accessed through the wired/wireless network (LAN or WLAN) with IP addresses, and the second information output devices 300 which are accessed through the local wireless network (ZigBee or Bluetooth) with unique device IDs, and determines a type of a user, i.e. a person with low vision or a blind person by identifying a kind of accessed communication (LAN/WLAN or ZigBee/Bluetooth) (S320). That is, the learning information server PC distinguishes the first information output devices 200 and the second information output devices 300, and manages the accessed information output devices individually or integratively.

The learning information server 100 identifies the kind of accessed communication (LAN/WLAN or ZigBee/Bluetooth), and determines whether or not a user is a person with low vision (S330).

As a result of the determination, when the first information output device 200 for the people with low vision has accessed to the learning information server 100, the learning information server 100 converts the inputted learning information into the learning information for people with low vision input by using the information conversion unit 130 (S340), and transmits the learning information for people with low vision to the first information output devices 200 through the wired/wireless network (LAN or WLAN) (S350).

As a result of the determination, when the second information output device 300 for blind people has accessed to the learning information server 100, the learning information server 100 converts the learning information inputted by the lecturing and authoring program into the haptic information for blind people (S360), and transmits the learning information for blind people, which may be converted to the haptic information, to the second information output devices (haptic electronic boards) 300 through the local wireless network (ZigBee or Bluetooth) (S370).

The lecturing and authoring program designates a page of learning data for visually impaired people by synchronizing with a page of specific learning information based on the same learning information upon lecture, Also, the people with low vision or the blind people transmit information of a current page to the learning information server 100 (S380).

The second information output device (haptic electronic board) 300 converts the learning information for blind people received from the learning information server 100 into the haptic information, controls the probes of a plurality of Tiny Ultrasonic Linear Actuators (TULAs) in a multi-arrangement, outputs the haptic information to the graphic output module, and transfers the haptic information to blind people using the graphic haptic electronic board (S390).

Figure 5:
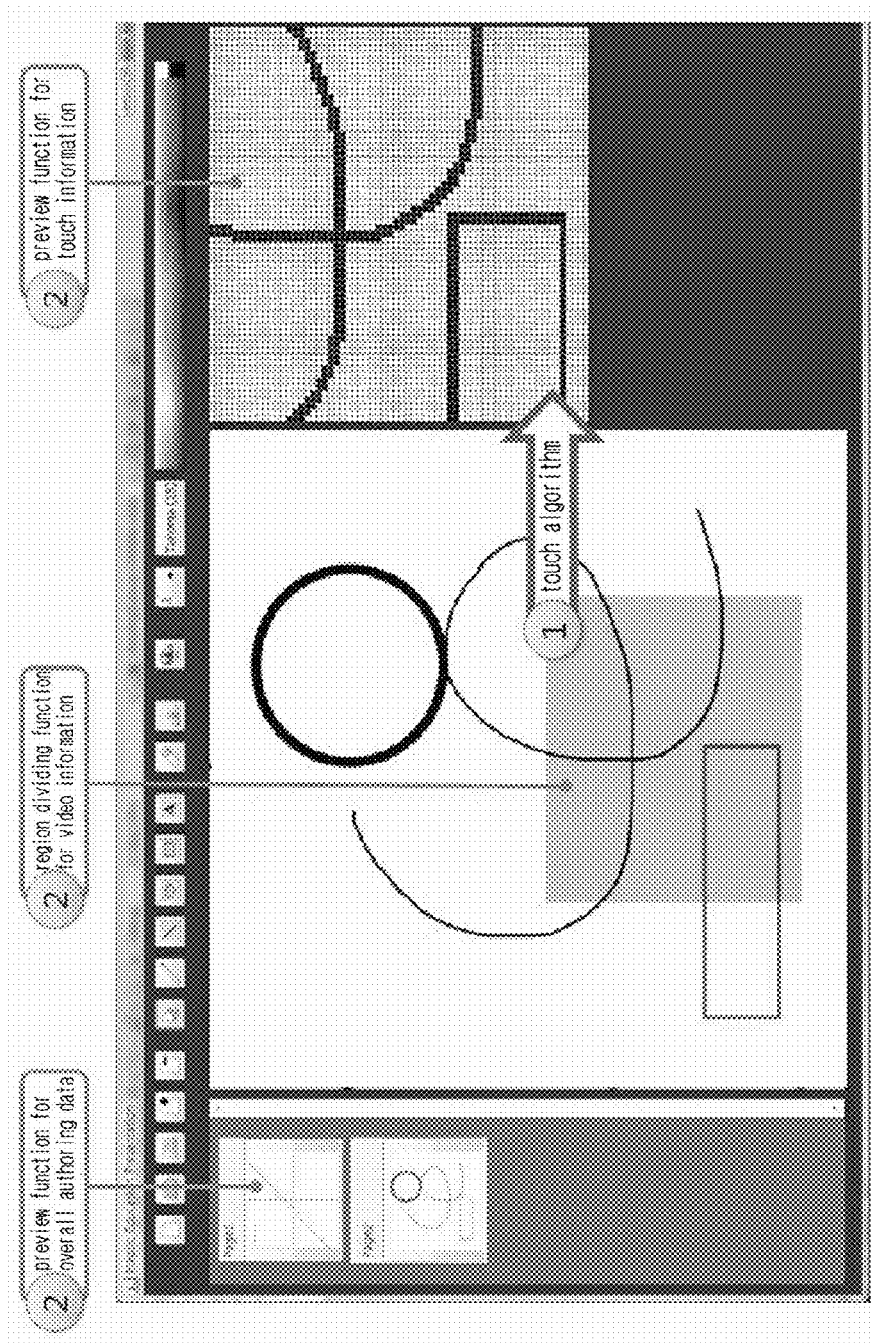
FIG. 5 is a screen illustrating the implementation of a touch algorithm of the lecturing and authoring program of the learning information for visually impaired people, a preview function of image information, and a region dividing function.

FIG. 5 is a screen illustrating the implementation of the touch algorithm of the lecturing and authoring program of the learning information for visually impaired people, a preview function of image information, and a region dividing function.

Figure 6:
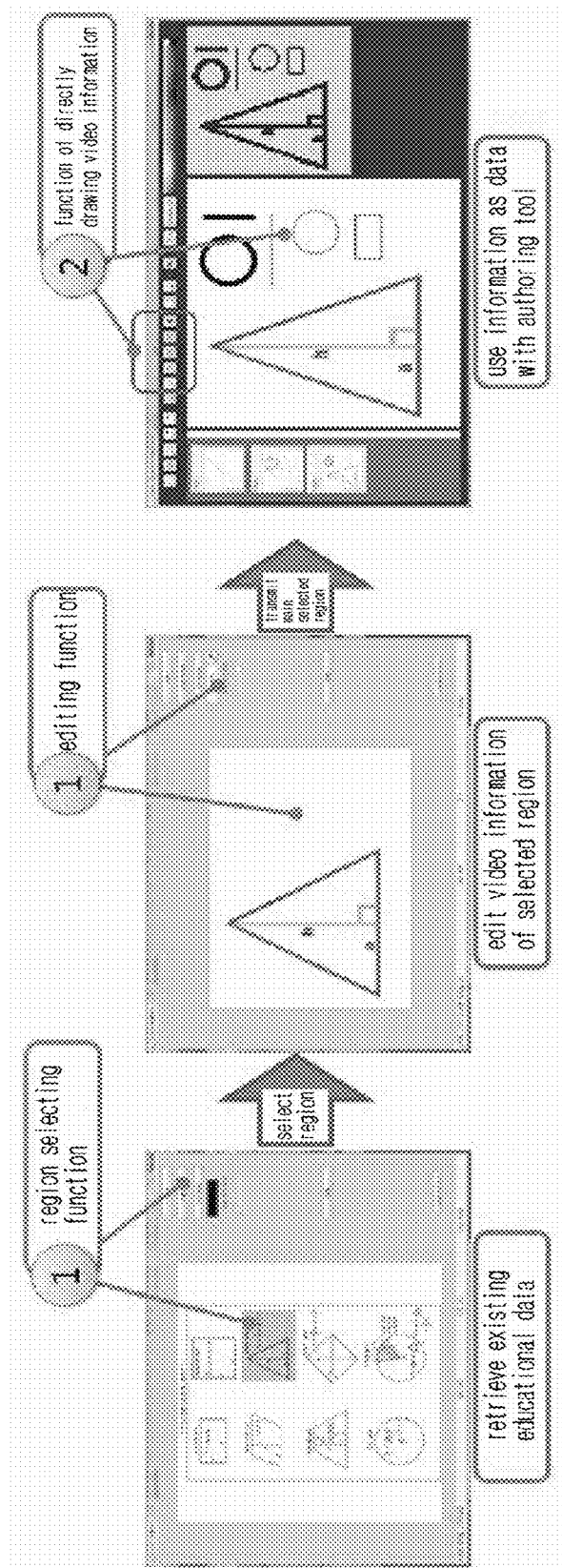
FIG. 6 is a screen illustrating a function of selecting a video region of the lecturing and authoring program of the learning information server for visually impaired people to be used for learning data, and a directly drawing function.

FIG. 6 is a screen illustrating a function of selecting a video region of the lecturing and authoring program of the learning information server for visually impaired people to be used for learning data, and a directly drawing function.

Figure 7:
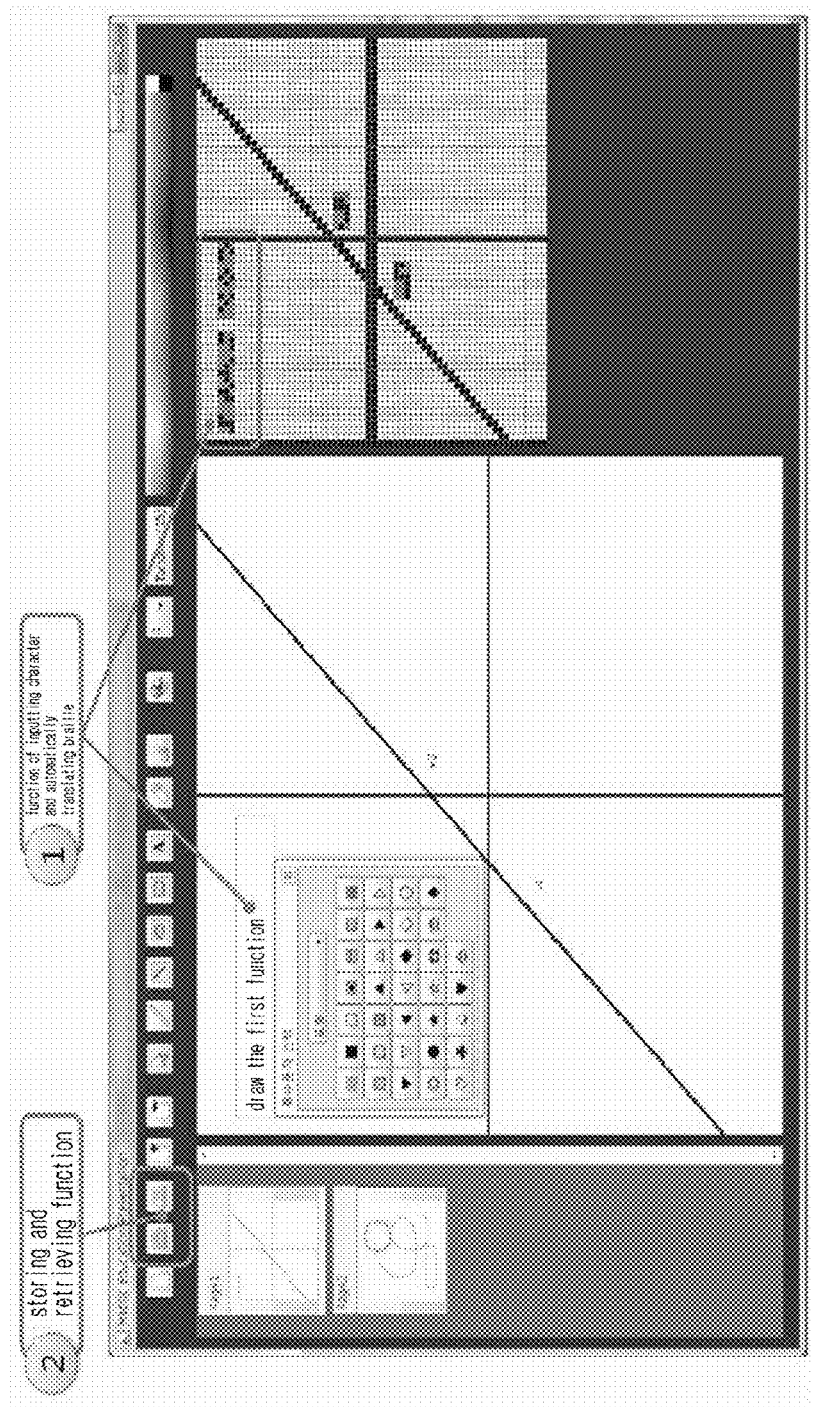
FIG. 7 is a screen illustrating a function related to a character of the lecturing and authoring program of the learning information server for visually impaired people and a function of retrieving learning data.

FIG. 7 is a screen illustrating a function related to a character of the lecturing and authoring program of the learning information server for visually impaired people and a function of retrieving learning data.

Figure 8:
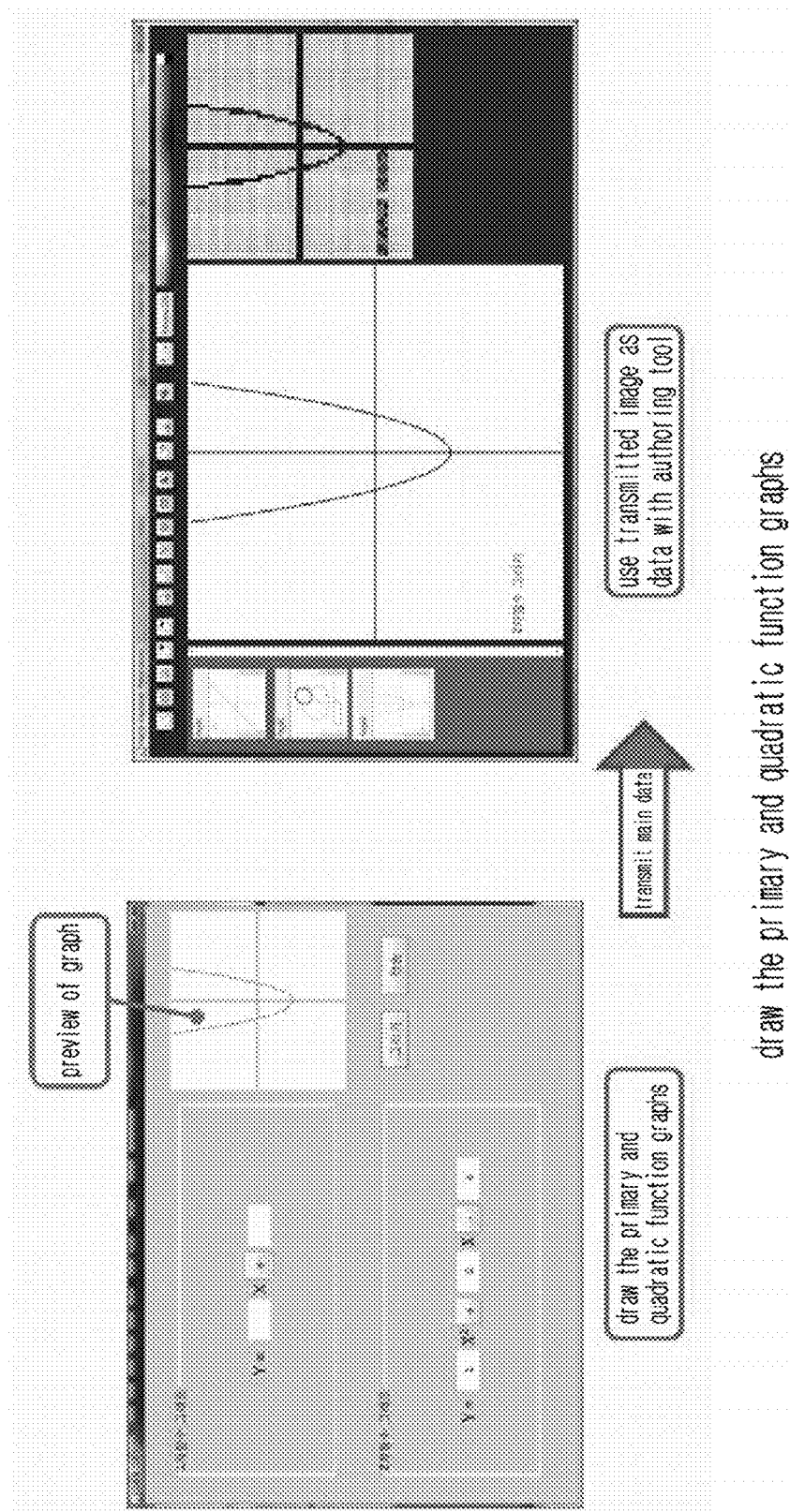
FIG. 8 is a screen illustrating a function of drawing the primary and quadratic function graphs of the lecturing and authoring program of the learning information server for visually impaired people.

FIG. 8 is a screen illustrating a function of drawing the primary and quadratic function graphs of the lecturing and authoring program of the learning information server for visually impaired people.

Figure 9:
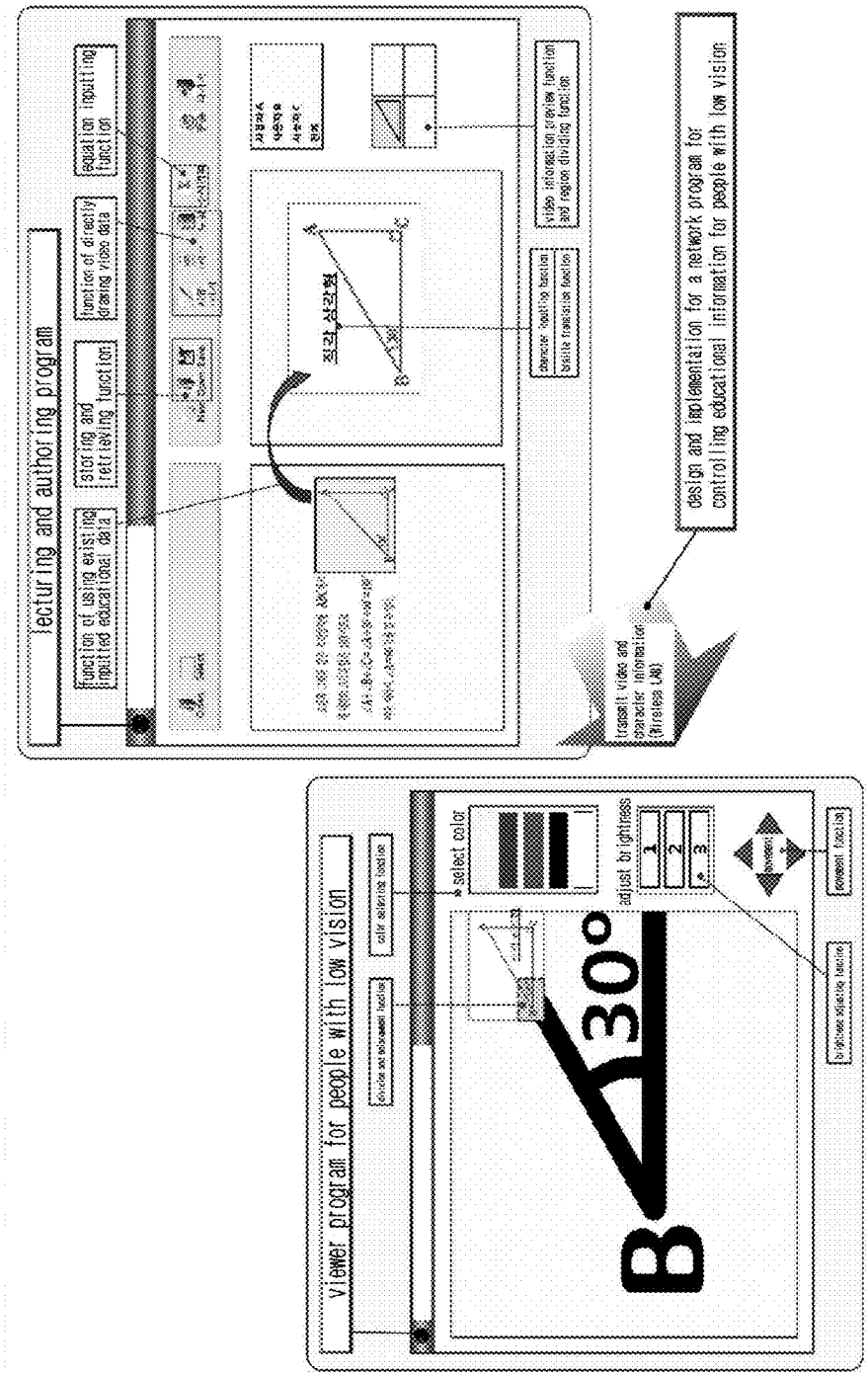
FIG. 9 is a screen illustrating the lecturing and authoring program based on a network of the learning information server for visually impaired people and the viewer program for people with low vision installed in a first information output device.

FIG. 9 is a screen illustrating the lecturing and authoring program based on a network of the learning information server for visually impaired people and the viewer program for people with low vision installed in a first information output device.

Figure 10:
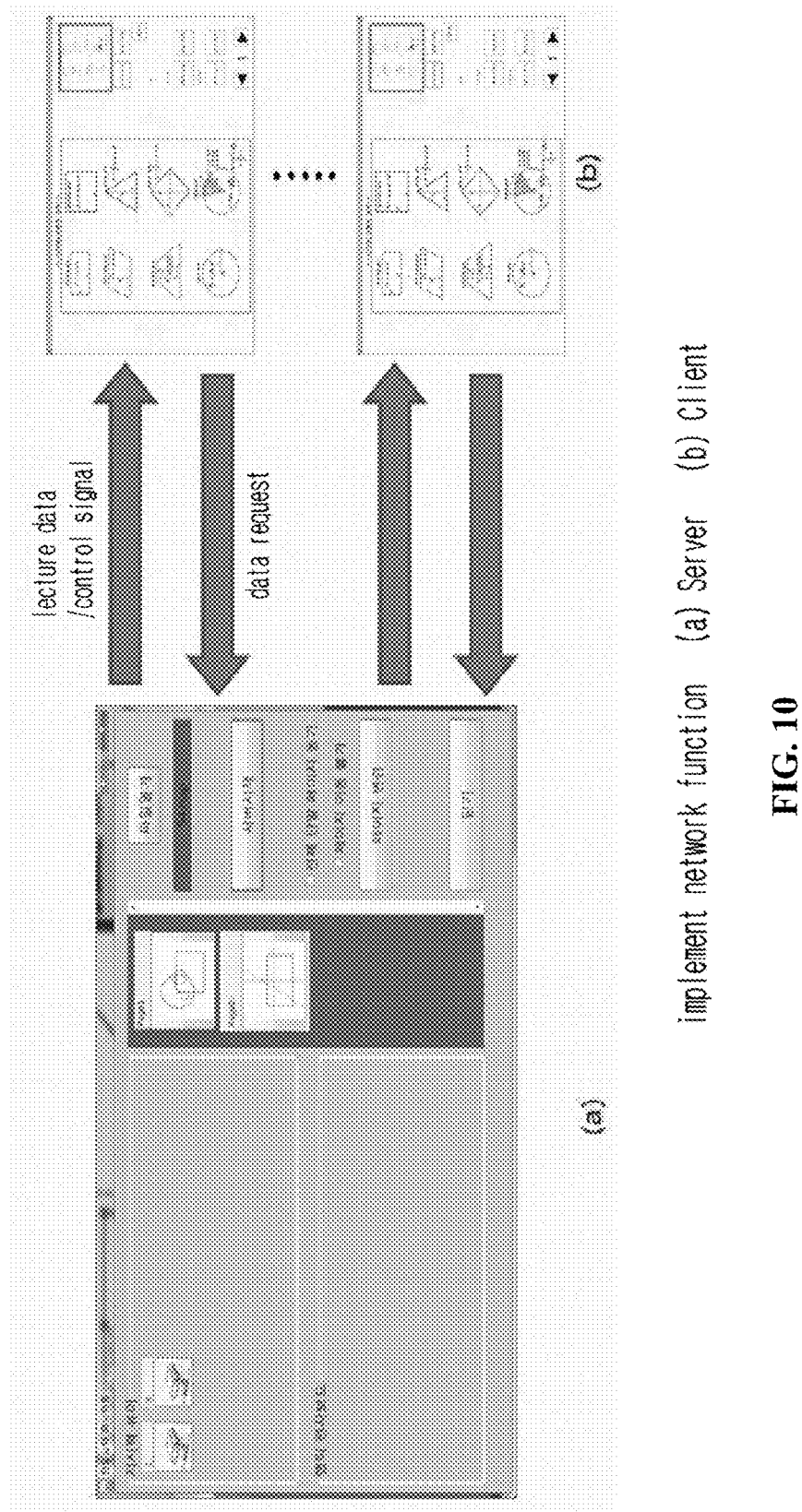
FIG. 10 is a screen illustrating a communication type of a lecture data control signal associated with a data request between the lecturing and authoring program of the learning information server for visually impaired people and the viewer program for people with low vision installed in the first information output device.

FIG. 10 is a screen illustrating a communication type of a lecture data control signal associated with a data request between the lecturing and authoring program of the learning information server for visually impaired people and the viewer program for people with low vision installed in the first information output device.

Figure 11:
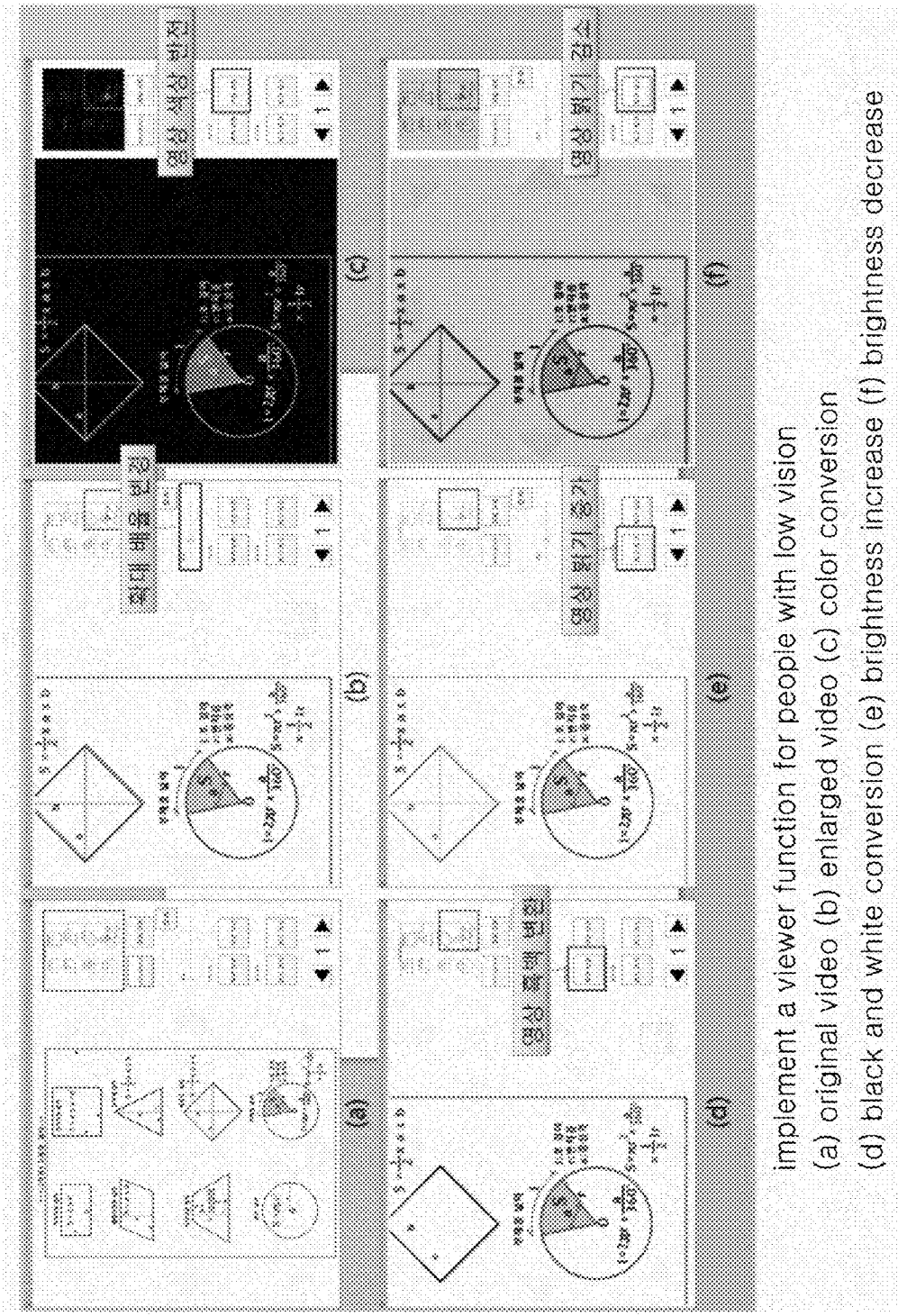
FIG. 11 is a screen illustrating a function (original image, enlarged image, color conversion, black and white conversion, brightness increase, brightness decrease) of the viewer program for people with low vision installed in the first information output device.

FIG. 11 is a screen illustrating a function (original image, enlarged image, color conversion, black and white conversion, brightness increase, brightness decrease) of the viewer program for people with low vision installed in the first information output device.

The learning information server 100 sets a size, a brightness, a contrast, and a combination of colors for the learning information displayed in a screen transmitted by the teacher on the basis of sights of the visually impaired people to the first information output device 200 so that the people with low vision can recognize the learning information for people with low vision. That is, the learning information server 100 performs functions of generating a graph, inputting and converting an equation, automatically converting to braille, managing students, and storing and retrieving the prepared data in consideration of characteristics of main subjects for blind people and a writing function which can be used as the teacher writes on a blackboard.

Also, the learning information server 100 manages functions of monitoring access states and output screens, transmitting individual learning data, and controlling to designate current output screens of the first information output device 200 and the second information output device 300 accessed through the network.

Further, the first information output device 200 and the second information output device 300 are controlled by the learning information server 100, and their screens may be automatically changed to a data screen which a teacher desires.

When the first information output device 200 or the second information output device 300 request to access to the learning information server 100 by using the unique device ID, the learning information server 100 provides a function of identifying an access state of the information output device having requested the access to the learning information server 100 by using a device state managing window. The first information output device 200 can identify a page of each device by using the device state managing window upon changing the page of the learning information. Also, the learning information server 100 may provide a function of synchronizing with a page of specific learning information in order to conduct the learning based on the same learning information.

Moreover, the learning information server 100 provides a function of scrolling the haptic information for the video and the braille in accordance with inputs of the first information output device 200 and the second information output device 300. Further, the learning information server 100 may provide a function of scrolling the haptic information for a limited resolution and a divided video data of the first information output device 200 and the second information output device 300. Furthermore, the learning information server 100 performs functions of storing the learning information transferred to the first information output device 200 and the second information output device 300 accessed through a network and controlling each device.

The learning information server 100 can be inputted specific learning information including a character, a number, an equation, a symbol, and a figure, by using the information input unit 110. For example, a manager can input information to the learning information server 100 by using an input device such as a mouse, a keyboard, or a tablet PC and the like. For example, the lecturing and authoring program (haptic edu) can draw by using a template of frequently used figures, including a straight line, a triangle, a circle, and a graph and the like. Further, the lecturing and authoring program (haptic edu) can set a unit of a two dimensional coordinate system and provide a function of drawing a graph such as drawing a function and a graph, and is implemented in such a manner that a detailed description and an annotation for a specific region of the input learning information are inputted in a form of a character. Further, the learning information server 100 may provide a function of automatically translating braille for the blind people.

The above mentioned inputted learning information is stored in the information storing unit 120 and provided by a "retrieving" function later. At that time, the lecturing and authoring program (haptic edu) provides a preview function by listing pages after reducing each of the pages. Further, a user stores the inputted learning information having a plurality of pages in one integrated file, and executes the retrieving function. The learning information is provided as a vector image, which has no distortion for the produced line and figure due to a resolution change. In addition, the lecturing and authoring program (haptic edu) provides an editing function such as a drawing function including deletion or addition of an unnecessary part.

The information conversion unit 130 of the learning information server 100 performs a function of converting the input learning information into image information which will be displayed in a terminal of the first information output device 200, or haptic information which will be output to the graph output unit of the second information output device 300 by using a transform algorithm of the input information. A producer can identify a type of the converted image information or haptic information in advance. Further, when a size of the learning information to be transmitted is large or a resolution of the learning information to be transmitted is high, the information conversion unit 130 provides a learning information region division function for people with low vision or blind people in which the producer directly divides a region of the learning information so as to transmit the divided region of the learning information to the first information output device 200 for people with low vision or the second information output device 300 for blind people.

The first information output device 200 includes the communication unit 210 for communicating with the server PC storing the learning information server 100 through the wired/wireless network (LAN or WLAN); and an application unit 220 for enlarging or reducing the learning information for people with low vision received from the learning information server 100 through the local wireless network (ZigBee or Bluetooth) and displaying the enlarged or reduced learning information in a terminal screen of a user.

That is, the learning information for people with low vision converted by the learning information server 100 is transmitted to the communication unit 210 of the first information output device 200, and output to the viewer program for people with low vision by the application unit 220.

The application unit 220 includes an information enlarging module 221 for enlarging a size of a screen displayed in a terminal of a user about the learning information for people with low vision, which has received the learning information from the learning information server 100 through the wired/wireless network (LAN or WLAN); an information reducing module 222 for reducing a size of a screen displayed in the terminal screen of the user about the learning information for people with low vision which has received the learning information from the learning information server 100; an information shifting module 223 for shifting a region a screen displayed in the terminal screen of the user about the learning information for people with low vision which has received the learning information from the learning information server

100; a color adjusting module 224 for adjusting a color displayed in the terminal screen of the user about the learning information for people with low vision which has received the learning information from the learning information server 100; and a brightness adjusting module 225 for adjusting a brightness of a screen displayed in the terminal screen of the user about the learning information for people with low vision which has received the learning information from the learning information server 100.

For example, the information enlarging module 221 provides a function of enlarging the transmitted visual learning information up to twofold to thirtyfold in order to enable the people with low vision to easily recognize the visual learning information.

The color adjusting module 224 performs functions of changing a color and adjusting black and white levels of the learning information for people with low vision who cannot distinguish a color.

The brightness adjusting module 225 adjusts video brightness for people with low vision who get easily tired when they view an overly dark or overly bright learning information video.

Also, the second information output device 300 receives learning information for blind people from the learning information server 100 through the ZigBee wireless communication, converts the received learning information into haptic information to output the converted haptic information, provides a function of moving a page by using a button or performing a page changing command in the learning information server 100, and supplies a high resolution. The second information output device 300 includes the communication unit 301 for providing to communicate with ZigBee or Bluetooth protocol, and uses the haptic electronic board for blind people.

The second information output device (haptic electronic board) 300 includes a communication unit 301 for receiving the learning information for blind people from the learning information server 100 through the local wireless communication network (ZigBee or Bluetooth); a master board 310 for receiving the learning information for blind people from the communication unit 301, providing a control command, and including a MCU (MicroControl Unit); at least one slave board 320 for being connected to the master board 310 and an SPI (Serial Peripheral Interface) bus, receiving the control command from the master board 310, and controlling ultrasonic actuators configured in a multi-arrangement; a plurality of Tiny Ultrasonic Linear Actuators (TULAs) 330 configured in a multi-arrangement; and a step down DC-DC converter 340 for being supplied with a power supply to convert a DC-DC voltage and providing the master board 310 and the slave board 320 with the converted DC-DC voltage.

The second information output device (haptic electronic board) 300 provides a function of expressing the learning information for blind people as haptic information by extracting an outline of video data by using an outline extracting algorithm of a three dimensional video data of a control program in an embedded system in order to enable blind people to recognize a character, a number, a symbol, a graph, a figure, and a video an image included in learning data for blind people, a function of expressing the learning information for blind people as three dimensional haptic information in a multi-arrangement based on the Tiny Ultrasonic Linear Actuators (TULAs) configured in a multi-arrangement, which can perform a linear motion by the graphic haptic electronic board, a function of configuring a touch cell of a 4 mm pitch in all directions to express continuous haptic information to visually impaired people, and a function of outputting the learning information for blind people, which is input at a rapid response rate lower than a maximum of 0.8 seconds in real time after receiving output information, as haptic information.

The second information output device (haptic electronic board) 300 can be implemented a graphic output function or a braille scroll function by using user input buttons such as top, bottom, left, right, front, and rear buttons, and increase the convenience of the user by manufacturing such that a screen can be shifted to a next screen or a previous screen.

A method for providing the learning information for visually impaired people based on the haptic electronic board installed in a computer provides a computer-readable storage medium having a program recorded thereon; where the program is to provide functions of: (a) inputting a character and an equation, a writing function, a function of drawing a graph and a figure, a function of retrieving existing data by using a lecturing and authoring program, inputting learning information for visually impaired people to a learning information server, distinguishing first information output devices accessed through a wired/wireless network to the learning information server by their IP addresses, and distinguishing second information output devices accessed through a local wireless network (ZigBee or Bluetooth) to the learning information server by their device IDs; (b) identifying a kind of network (LAN/WLAN or ZigBee/Bluetooth) accessing the learning information server, and determining whether or not a user is a person with low vision; (c) as a result of the determination, when a first information output device for people with low vision accesses to the learning information server, converting inputted learning information into learning information for people with low vision by using an information converting unit, and transmitting the learning information for people with low vision from the learning information server to the first information output device through the wired/wireless network (LAN or WLAN); (d) as a result of the determination, when a second information output device for blind people accesses to the learning information server, converting inputted learning information into haptic information for blind people, and transmitting the learning information for blind people, which can be transferred as the haptic information, from the learning information server to the second information output device (haptic electronic board) through the local wireless network (ZigBee or Bluetooth); and (e) designating a page of learning data for visually impaired people by synchronizing with a page of specific learning information based on identical learning information by the lecturing and authoring program, or synchronizing with a learning page by transmitting information of a current page to the learning information server by the people with low vision or the blind people.

Figure 12:
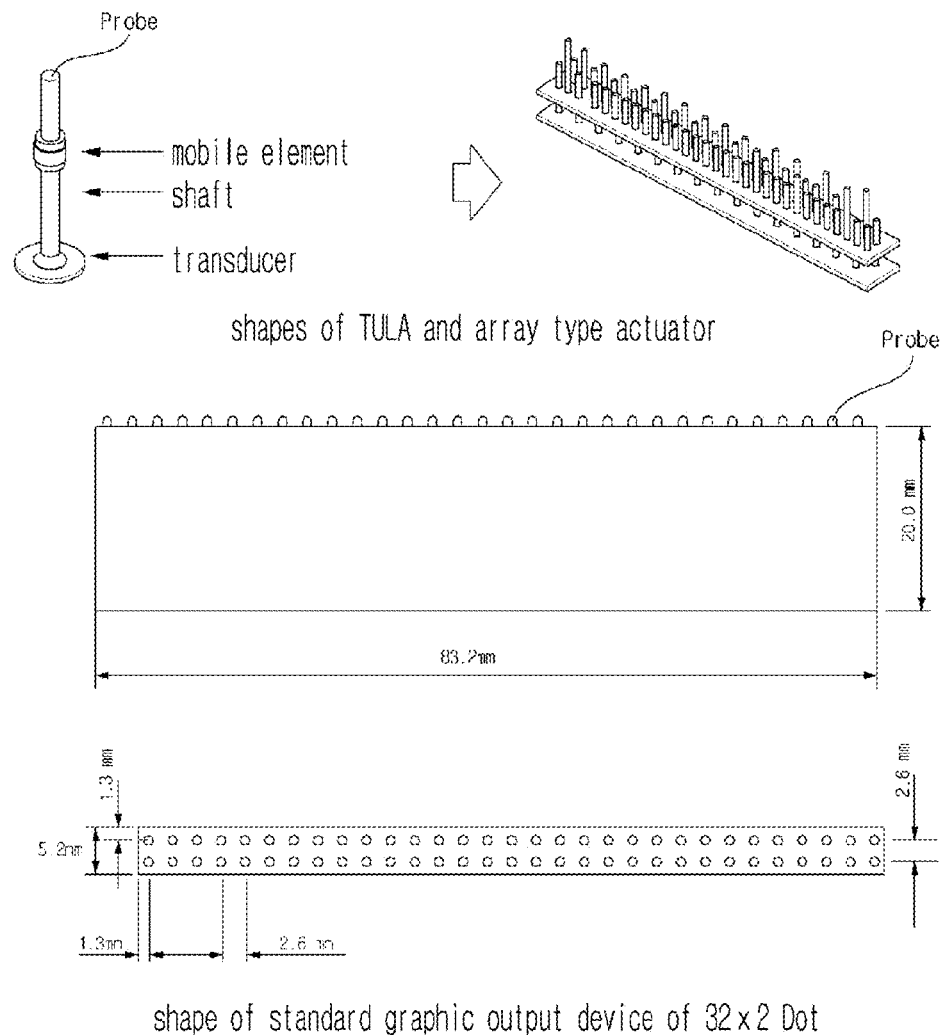
FIG. 12 illustrates shapes of a Tiny Ultrasonic Linear Actuator (TULA) and an array of the TULAs of a second information output device (haptic electronic board), and a size and a shape of a standard graphic output device of 32×2 Dot including four 8×2 standard graphic output modules (32× 2) as an embodiment.

FIG. 12 illustrates shapes of the Tiny Ultrasonic Linear Actuator (TULA) and an array of the TULAs of the second information output device (haptic electronic board), and a size and a shape of a standard graphic output device of 32×2 Dot including four 8×2 standard graphic output modules (32× 2) as an embodiment.

The array type actuators of the Tiny Ultrasonic Linear Actuators (TULAs) of the second information output device (haptic electronic board) 300 has a two-step structure of TULA and is configured in a multi-arrangement of actuators of TULAs. The array type actuators can be manufactured in a tiny and light-weight structure and can establish a multiline structure. The second information output device (haptic electronic board) 300, which has a size of 83.2 mm×5.2 mm×20 mm, supports a holding torque of 10 g·f (gram force) and guarantees a durability of the haptic electronic board for more than fifty thousand touches since the probes of the Tiny Ultrasonic Linear Actuators (TULAs) should be strong enough to endure the touch of a user so that a blind person can recognize information by using the sense of touch.

The Tiny Ultrasonic Linear Actuator (TULA) is composed of a probe of the TULA, which corresponds to a part that blind people recognize braille with a touch; a mobile element for fixing the probe; a shaft for moving the mobile element up and down for a vertical movement in order to transfer a contact intensity signal related to the learning information for blind people; and a transducer for controlling the vertical movement when a torque is received so as to drive the TULA.

The second information output device (haptic electronic board) 300 is manufactured such that a distance between the probes is set to 2.6 mm so that a visually impaired person can recognize in highest accuracy and delicately transfer learning information including equation, figure, graph, and image information as the haptic information to blind people.

Figure 13:
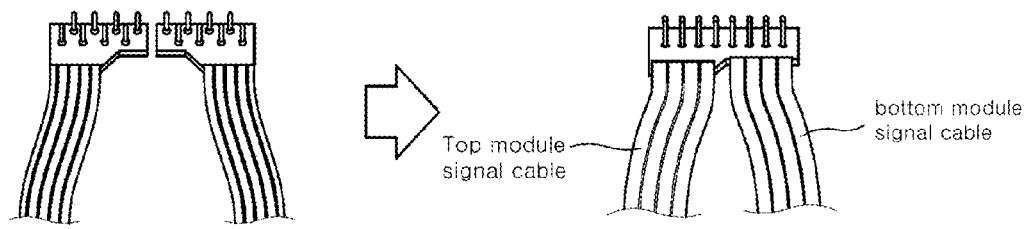
FIG. 13 illustrates a basic 8×2 standard graphic output module of the haptic electronic board which is composed of a 4×2 standard graphic output module having a four-line top module signal cable and a four-line bottom module signal cable respectively and is formed a two-steps structure including top and bottom structure to implement tiny and lightweight array type actuators upon a manufacturing process of the array type actuator after developing the array type TULA (Tiny Ultrasonic Linear Actuator)
Figure 13:
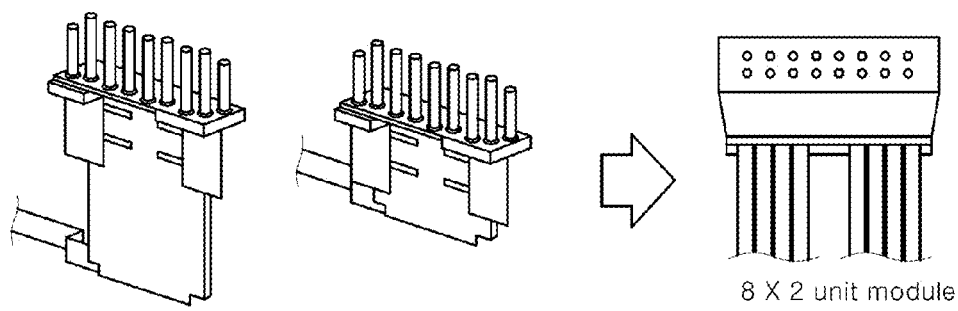

FIG. 13 illustrates a basic 8×2 standard graphic output module of the haptic electronic board which is composed of a 4×2 standard graphic output module having a four-line top module signal cable and a four-line bottom module signal cable respectively and is formed a two-steps structure including top and bottom structure to implement tiny and lightweight array type actuators upon a manufacturing process of the array type actuator after developing the array type TULA (Tiny Ultrasonic Linear Actuator).

A module of the array type piezoelectric actuator is manufactured such that it has a multi-structure (double two-steps structure) in order to improve the accuracy of the module by implementing in such a manner that a distance between the probes of the TULA of the graphic output module of the second information output device (haptic electronic board) 300 is set to a value lower than 2.7 mm in order to enable blind people to delicately detect the learning information for blind people including braille, equation, symbol, figure, graph, and image information for visually impaired people as the haptic information.

Figure 14:
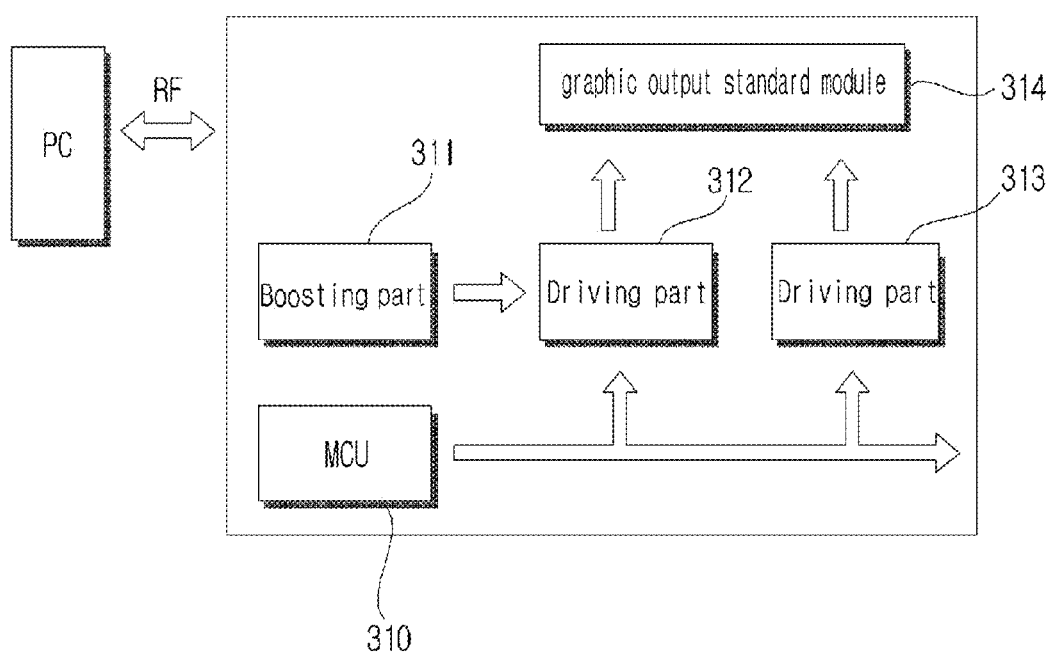
FIG. 14 is a block diagram of a driving circuit of a standard graphic output module of the second information output device (haptic electronic board)

FIG. 14 is a block diagram of a driving circuit of a standard graphic output module of the second information output device (haptic electronic board).

The driving circuit of the standard graphic output module of the haptic electronic board comprises an MCU for controlling the overall functions of the haptic electronic board; a boosting part, a driving part, an FPGA for controlling on/off states and a vertical movement of the TULA; and a graphic output module for converting the learning information to the contact intensity signal by using the touch algorithm of a character, a number, an equation, a symbol, a figure, and an image included in the learning information for blind people and outputting the converted contact intensity signal.

Figure 15:
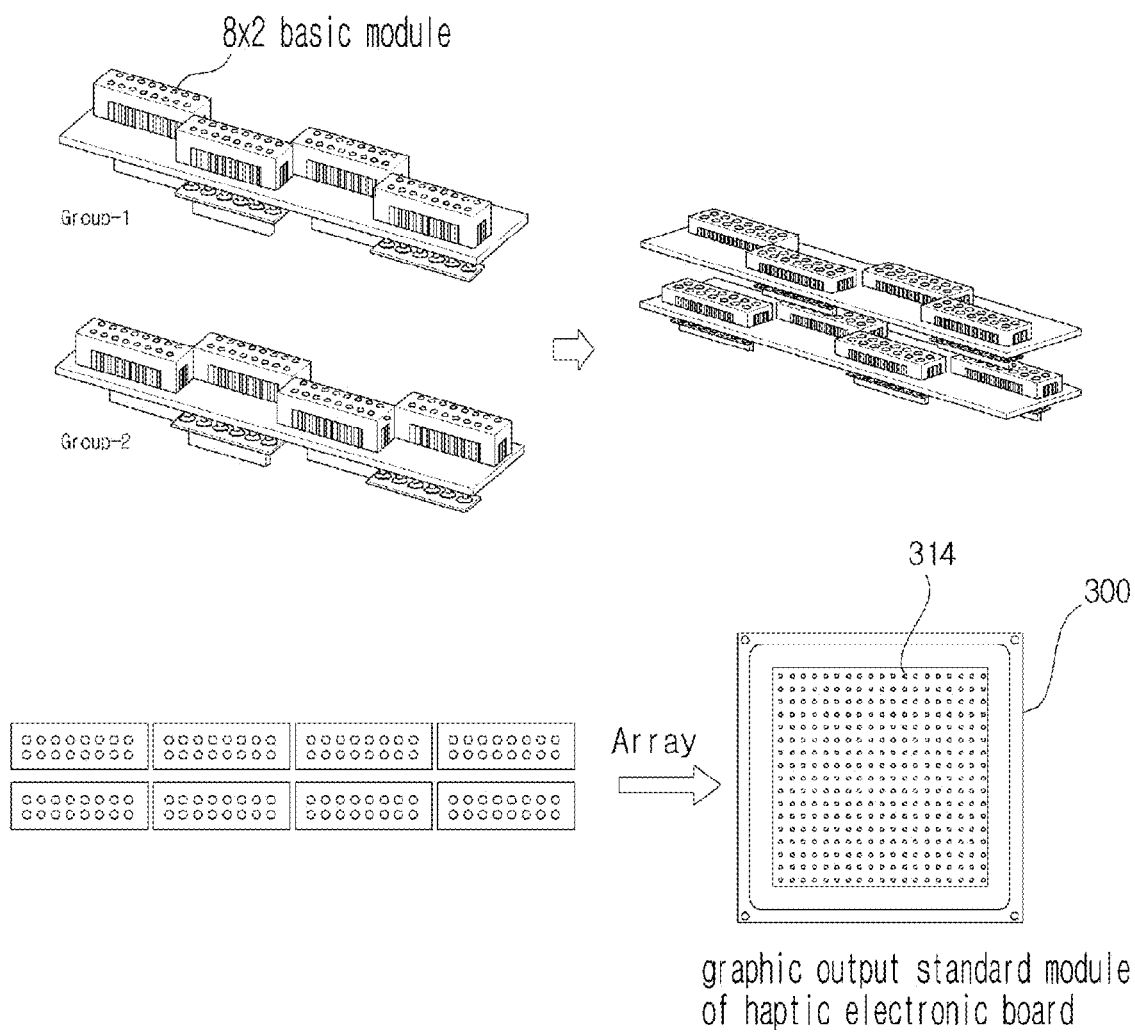
FIG. 15 illustrates a graphic output standard module of the haptic electronic board including the combination of basic 8×2 standard graphic output modules having probes for each of two groups of haptic electronic board.

FIG. 15 illustrates a graphic output standard module 314 of the haptic electronic board 300 including the combination of basic 8×2 standard graphic output modules having the probes for each of two groups of the haptic electronic board.

Figure 16:
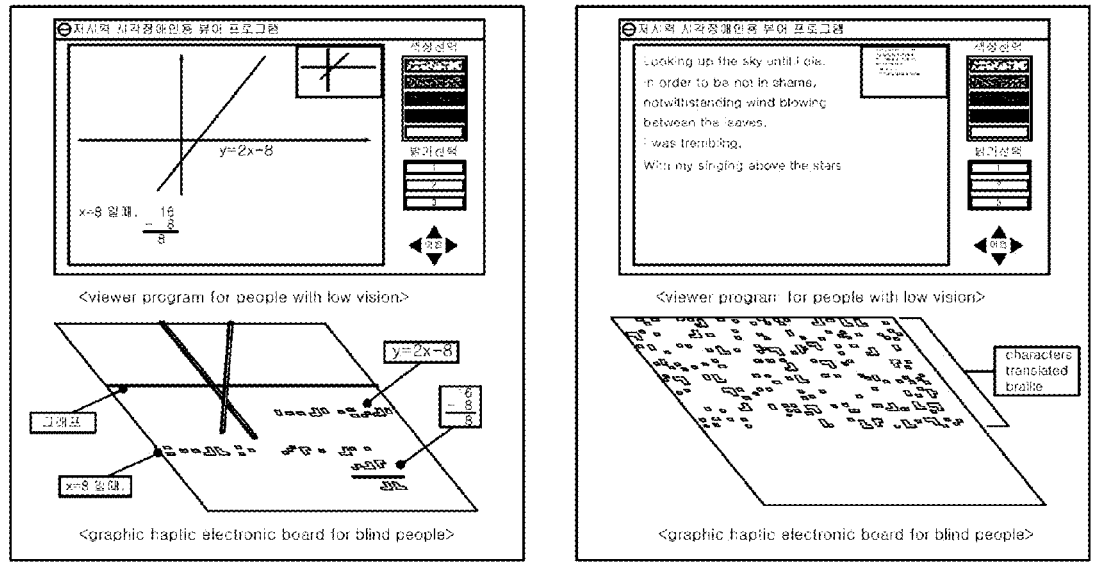
FIGS. 16A and 16B are screens illustrating haptic information related to learning information for blind people displayed in the graphic output module of the second information output device (haptic electronic board).

FIGS. 16A and 16B are screens illustrating the haptic information related to the learning information for blind people output to the graphic output module of the second information output device (haptic electronic board).

The second information output device (haptic electronic board) 300 accesses to the learning information server 100 through the wireless network (ZigBee or Bluetooth) by using the unique device ID, and receives the learning information for blind people from the learning information server 100. Further, the second information output device (haptic electronic board) 300 converts the learning information for blind people into haptic information by using the touch algorithm of a character, a number, a symbol, a figure, a graph, and an image, controls the probes of a plurality of TULAs disposed in a multi-arrangement by a control of the MCU, outputs the haptic information to the graphic output module, and transfers the haptic information in order to enable blind people to sense the haptic information through their sense of touch by hands.

For example, upon learning the blind people by using the haptic electronic board, the blind people can learn an equation of y=2x−8, and a graph and a description for the equation by sensing protruded probes of a plurality of TULAs disposed in a multi-arrangement of the graphic output module of the haptic electronic board so as to the equation of y=2x−8 and the description through the sense of touch of their hands.

The learning information server 100 can be implemented a transmission mode for transmitting the inputted learning information to the first information output device 200 and the second information output device 300 through the network generally in a 1:N mode, or selecting a device ID of an individual information output device and transmitting the inputted learning information to the information output device corresponding to the selected device ID in a 1:1 mode, if necessary.

A prototype of the system for providing the learning information for visually impaired people based on the haptic electronic board using the local wireless communication (ZigBee or Bluetooth) according to the present invention is even more effective and convenient for improving the understanding of visually impaired people in a case where educational data is described while the haptic information is provided together with a voice output in comparison to a case where educational data including video data is described while only a voice associated with characters is provided, in an evaluating process of the visually impaired people.

The system and method for providing the learning information for visually impaired people based on the haptic electronic board according to the present invention is inputted learning information including equation, symbol, picture, figure, graph, and image information as well as character information to a learning information server through a lecturing and authoring program and re-configures the learning information to image information for people with low vision in order to enable the people with low vision to easily recognize the information, automatically converts the learning information into haptic information for blind people in order to enable the blind people to easily recognize the learning information in real time, and transmits the learning information stored in the learning information server to first information output devices (PCs) for people with low vision, in which a viewer program for people with low vision is installed, through the network and/or to second information output devices (haptic electronic boards) for blind people through the local wireless network (ZigBee or Bluetooth) in real time. Therefore, the learning information for people with low vision and the haptic information for blind people may be transmitted to both people with low vision and blind people having different degrees of visual impairments in accordance with each visual impairment rating.

In order to maximize a special education effect for visually impaired people such as people with low vision and blind people and so forth, the system for providing learning information for visually impaired people converts the learning information including character, equation, symbol, figure, graph, and image information into the haptic information, and simultaneously transmits the learning information for people with low vision to computers used by the people with low vision through the wired/wireless network (LAN or WLAN)

and the learning information for blind people to a plurality of haptic electronic boards through the local wireless network such as ZigBee or Bluetooth. The haptic electronic board converts the learning information into the haptic information and may be used as an educational assistive engineering system based on a graphic haptic electronic board, which transmits the converted haptic information to visually impaired people.

As described above, the method according to the present invention may be implemented as a program and stored to a recording medium (CD-ROM, RAM, ROM, memory card, hard disk, and optical magnetic disk, and the like) in a readable form by using a computer software.

While the present invention has been particularly shown and described with reference to exemplary embodiments thereof, it will be understood by those skilled in the art that various changes in form and details may be made therein without departing from the spirit and the scope of the present invention as defined by the appended claims.

What is claimed is:

1. A system for providing learning information for visually impaired people based on a haptic electronic board, the system comprising:
    a first information output device which is a PC for people with low vision for accessing to a learning information server in conjunction with a lecturing and authoring program to receive learning information for people with low vision, wherein said first information output device includes a LAN or WLAN communication unit and having a viewer program for people with low vision installed therein and provides functions of information enlarging, reducing and shifting, color adjusting and brightness adjusting; and
    a second information output device which is a haptic electronic board for blind people for accessing to the learning information server through a local wireless network using a unique device ID assigned thereto, receiving learning information for blind people from the learning information server, converting the learning information for blind people into haptic information, controlling probes of a plurality of Tiny Ultrasonic Linear Actuators disposed in a multi-arrangement, outputting the haptic information to a graphic output module, and transferring the haptic information to visually impaired people,
    wherein the lecturing and authoring program and the learning information server are installed in a learning information server PC equipped with a network connection unit using LAN or WLAN and a wireless communication interface unit using the local wireless network, and the learning information server converts learning information into learning information for people with low vision including character, equation, symbol, figure, graph, and image information produced, or learning information for blind people, which may be transferred in a form of haptic information by using an automatic haptic information conversion technology, and transmits the learning information for people with low vision or the learning information for blind people, which can be transferred as haptic information, to one or more information output devices through LAN or WLAN or a local wireless network in a 1:N or a 1:1 transmission mode, or synchronize with a learning page by transmitting information of a current page from the learning information server in accordance with the lecturing and authoring program,
    wherein said second information output device includes a communication unit for receiving the learning information for blind people from the learning information server through the local wireless communication; a master board for receiving the learning information for blind people from the communication unit to provide a control command, and including an MCU; at least one slave board for receiving the control command from the master board, and controlling ultrasonic actuators arranged in a multi-arrangement, and being connected with the master board through an SPI bus; a plurality of Tiny Ultrasonic Linear Actuators disposed in a multi-arrangement; and a step down DC-DC converter for being supplied with a power supply, converting a DC-DC voltage, and providing the converted DC-DC voltage to the master board and the slave board, wherein a distance between probes of the TULA of the graphic output module of said second information output device is set to a value lower than 2.7 mm, and wherein a module of an array type piezoelectric actuator is manufactured such that it has a multi-structure of TULA and is configured in a multi-arrangement of actuators of TULAs wherein said second information output device includes a graphic information function or a brail scroll function by using user input buttons including top, bottom, left, right, front and rear buttons and is configured so that its screen can be moved to a next screen or a previous screen.

2. The system of claim 1, wherein the learning information server comprises:
    an information input unit for receiving an input of the learning information including equation, symbol, figure, graph, and image information as well as character information produced by the lecturing and authoring program;
    an information storing unit for storing information inputted from the information input unit;
    an information converting unit for converting the learning information inputted from the information input unit into learning information for people with low vision and learning information for blind people respectively, which may be transferred in a form of the haptic information; and
    a wireless communication interface unit for providing the learning information for blind people when the learning information server communicates with a plurality of second information output devices through the local wireless network.

3. The system of claim 2, wherein the learning information server further comprises:
    a network connection unit for transmitting the learning information for people with low vision to the first information output device, in which the viewer program for people with low vision is installed, when the learning information server PC communicates with the first information output devices through the wired/wireless network using LAN or WLAN.

4. The system of claim 2, wherein the first information output device comprises:
    a communication unit for communicating with the learning information server storing the learning information through the wired/wireless network using LAN or WLAN; and
    an application unit for displaying the learning information for people with low vision received from the learning information server on a terminal screen of a user.

5. The system of claim 1, wherein the first information output device comprises:

a communication unit for communicating with the learning information server storing the learning information through the wired/wireless network using LAN or WLAN; and an application unit for displaying the learning information for people with low vision received from the learning information server on a terminal screen of a user, wherein the application unit provides functions of information enlarging, reducing and shifting, color adjusting and brightness adjusting.

6. The system of claim 5, wherein the application unit comprises:

an information enlarging module for enlarging a size of a screen displayed in the terminal screen of the user about the learning information for people with low vision received from the learning information server through the network;

an information reducing module for reducing a size of a screen displayed in the terminal screen of the user about the learning information for people with low vision received from the learning information server;

an information shifting module for shifting a region of a screen displayed in the terminal screen of the user about the learning information for people with low vision received from the learning information server;

a color adjusting module for adjusting color of an image or a video displayed on the terminal screen of the user about the learning information for people with low vision received from the learning information server; and a brightness adjusting module for adjusting a brightness of a screen displayed in the terminal screen of the user about the learning information for people with low vision received from the learning information server.

7. The system of claim 1, wherein the learning information server implements a network program for controlling the learning information for people with low vision, controls each of the viewer programs for people with low vision set by a unique identification code, transmits the learning information for people with low vision including video and character information produced by distinguishing the viewer program for people with low vision, and transmits the learning information for people with low vision produced by the lecturing and authoring program in a 1:N mode based on a wireless LAN, or selectively transmits to each of the information output devices in a 1:1 mode, if necessary.

8. The system of claim 1, wherein the lecturing and authoring program provides:

a character input function including a character, a number, an equation, a symbol specialized for each subject of blind people; a function of inputting a detailed description and an annotation regarding a specific region of produced video information; an automatic braille translating function for blind people; a function of implementing a touch algorithm of video data suitable for said second information output device for blind people; a free drawing function using an input device associated with a mouse, a keyboard, or a tablet PC, a drawing function using a template of a frequently used figure associated with a straight line, a triangle, a circle, or a graph, a function of directly drawing image information for setting a unit of a two dimensional coordinate system and providing a function of drawing a graph; a preview and a region dividing function of video information of previously identifying a form of haptic information, which will be displayed in the graphic output module of said second information output device that is haptic electronic board, by using the touch algorithm of the image and directly dividing the region to transfer the divided region when a size of image information to be transmitted is large or a resolution of the image information is high; and a function of storing and retrieving the produced learning information.

9. The system of claim 1, wherein the viewer program for people with low vision is used in said first information output device, provides a function of outputting a character, a number, an equation, and a symbol, a function of dividing and enlarging a screen, a function of shifting a screen, a function of selecting a color, a function of adjusting a brightness, a function of adjusting a contrast, and provides people with low vision with learning information for people with low vision including character, equation, symbol, figure, graph and image information received from the learning information server.

10. A method for providing learning information for visually impaired people based on a haptic electronic board, the method comprising:

providing a function of inputting a character and an equation, a writing function, a function of drawing a graph and a figure, a function of retrieving existing data, inputting learning information for visually impaired people to a learning information server by using a lecturing and authoring program, distinguishing first information output devices accessed through a wired/wireless network to the learning information server by their IP addresses, and distinguishing second information output devices accessed through a local wireless network to the learning information server by their device IDs;

identifying a kind of network accessing the learning information server, and determining whether a user is a person with low vision;

as a result of the determination, when a first information output device for people with low vision accesses to the learning information server, converting inputted learning information into learning information for people with low vision by using an information converting unit, and transmitting the learning information for people with low vision from the learning information server to the first information output device through the wired/wireless network;

as a result of the determination, when a second information output device for blind people accesses the learning information server, converting inputted learning information into haptic information for blind people, and transmitting the learning information for blind people, which can be transferred as the haptic information, from the learning information server to the second information output device through the local wireless network; and designating a page of learning data for visually impaired people by synchronizing with a page of specific learning information based on identical learning information by the lecturing and authoring program, or synchronizing with a learning page by transmitting information of a current page to the learning information server by the people with low vision or the blind people, wherein said second information output device includes a master board and at least one slave board, a Serial Peripheral interface (SPI) bus, a step down DC-DC converter and a plurality of Tiny Ultrasonic Linear Actuators (TULAs) disposed in a multi-arrangement, and converts the learning information for blind people received from the learning information server into the haptic information, controls probes of a plurality of Tiny Ultrasonic Linear Actuators (TULAs) disposed in a multi-arrangement, outputs the haptic information to a graphic output module, and transfers the haptic information to the blind people using the graphic haptic electronic board.

* * * * *